United States Patent
Hubbell et al.

(10) Patent No.: US 10,832,796 B2
(45) Date of Patent: *Nov. 10, 2020

(54) SYSTEM, METHOD, AND COMPUTER SOFTWARE PRODUCT FOR GENOTYPE DETERMINATION USING PROBE ARRAY DATA

(71) Applicant: Affymetrix, Inc., Santa Clara, CA (US)

(72) Inventors: Earl A. Hubbell, Palo Alto, CA (US); Simon Cawley, Oakland, CA (US)

(73) Assignee: Affymetrix, Inc., Carlsbad, CA (US)

( * ) Notice: Subject to any disclaimer, the term of this patent is extended or adjusted under 35 U.S.C. 154(b) by 589 days.

This patent is subject to a terminal disclaimer.

(21) Appl. No.: 15/680,168

(22) Filed: Aug. 17, 2017

(65) Prior Publication Data

US 2018/0039727 A1 Feb. 8, 2018

Related U.S. Application Data

(60) Division of application No. 13/468,604, filed on May 10, 2012, now Pat. No. 9,760,675, which is a continuation of application No. 12/123,463, filed on May 19, 2008, now Pat. No. 8,200,440.

(60) Provisional application No. 60/938,757, filed on May 18, 2007.

(51) Int. Cl.
*G01N 33/48* (2006.01)
*G16B 20/00* (2019.01)
*G16B 25/00* (2019.01)
*G16B 40/00* (2019.01)

(52) U.S. Cl.
CPC .............. *G16B 20/00* (2019.02); *G16B 25/00* (2019.02); *G16B 40/00* (2019.02)

(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,242,974 A | 9/1993 | Holmes |
| 5,252,743 A | 10/1993 | Barrett et al. |
| 5,324,633 A | 6/1994 | Fodor et al. |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,427,932 A | 6/1995 | Weier et al. |
| 5,447,841 A | 9/1995 | Gray et al. |
| 5,451,683 A | 9/1995 | Barrett et al. |
| 5,472,842 A | 12/1995 | Stokke et al. |
| 5,482,867 A | 1/1996 | Barrett et al. |
| 5,491,074 A | 2/1996 | Aldwin et al. |
| 5,527,681 A | 6/1996 | Holmes |
| 5,541,061 A | 7/1996 | Fodor et al. |
| 5,547,839 A | 8/1996 | Dower et al. |
| 5,550,215 A | 8/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |
| 5,624,711 A | 4/1997 | Sundberg et al. |
| 5,631,734 A | 5/1997 | Stern et al. |
| 5,633,365 A | 5/1997 | Stokke et al. |
| 5,665,549 A | 9/1997 | Pinkel et al. |
| 5,721,098 A | 2/1998 | Pinkel et al. |
| 5,795,716 A | 8/1998 | Chee et al. |
| 5,800,992 A | 9/1998 | Fodor et al. |
| 5,801,021 A | 9/1998 | Gray et al. |
| 5,830,645 A | 11/1998 | Pinkel et al. |
| 5,831,070 A | 11/1998 | Pease et al. |
| 5,834,758 A | 11/1998 | Trulson et al. |
| 5,837,832 A | 11/1998 | Chee et al. |
| 5,840,482 A | 11/1998 | Gray et al. |
| 5,856,092 A | 1/1999 | Dale et al. |
| 5,856,097 A | 1/1999 | Pinkel et al. |
| 5,856,101 A | 1/1999 | Hubbell et al. |
| 5,858,659 A | 1/1999 | Sapolsky et al. |

(Continued)

FOREIGN PATENT DOCUMENTS

| | | |
|---|---|---|
| EP | 1 019 536 B1 | 10/2004 |
| WO | 95/11995 A1 | 5/1995 |

(Continued)

OTHER PUBLICATIONS

Wang et al., "Large-Scale Identification, Mapping, and Genotyping of Single-Nucleotide Polymorphisms in the Human Genome," Science, May 1998, vol. 280, pp. 1077-1082.

Wodicka et al., "Genome-wide expression monitoring in *Saccharomyces cerevisiae*," Nature Biotechnology, 1997, vol. 15, pp. 1359-1367.

Zhou et al., "Match-Only Integral Distribution (MOID) Algorithm for high-density oligonucleotide array analysis," BMC Bioinformatics, Jan. 2002, vol. 3, Issue 3, pp. 1-15.

(Continued)

*Primary Examiner* — Anna Skibinsky

(74) *Attorney, Agent, or Firm* — Mauriel Kapouytian Woods LLP; Elaine K. Lee; Michael Mauriel

(57) ABSTRACT

An embodiment of a method of analyzing data from processed images of biological probe arrays is described that comprises receiving a plurality of files comprising a plurality of intensity values associated with a probe on a biological probe array; normalizing the intensity values in each of the data files; determining an initial assignment for a plurality of genotypes using one or more of the intensity values from each file for each assignment; estimating a distribution of cluster centers using the plurality of initial assignments; combining the normalized intensity values with the cluster centers to determine a posterior estimate for each cluster center; and assigning a plurality of genotype calls using a distance of the one or more intensity values from the posterior estimate.

29 Claims, 18 Drawing Sheets

(56) References Cited

U.S. PATENT DOCUMENTS

| | | |
|---|---|---|
| 5,871,928 A | 2/1999 | Fodor et al. |
| 5,889,165 A | 3/1999 | Fodor et al. |
| 5,902,723 A | 5/1999 | Dower et al. |
| 5,928,870 A | 7/1999 | Lapidus et al. |
| 5,936,324 A | 8/1999 | Montagu |
| 5,959,098 A | 9/1999 | Goldberg et al. |
| 5,965,362 A | 10/1999 | Pinkel et al. |
| 5,968,740 A | 10/1999 | Fodor et al. |
| 5,974,164 A | 10/1999 | Chee |
| 5,976,790 A | 11/1999 | Pinkel et al. |
| 5,981,185 A | 11/1999 | Matson et al. |
| 5,981,956 A | 11/1999 | Stern |
| 6,013,449 A | 1/2000 | Hacia et al. |
| 6,020,135 A | 2/2000 | Levine et al. |
| 6,025,601 A | 2/2000 | Trulson et al. |
| 6,027,880 A | 2/2000 | Cronin et al. |
| 6,033,860 A | 3/2000 | Lockhart et al. |
| 6,040,138 A | 3/2000 | Lockhart et al. |
| 6,040,193 A | 3/2000 | Winkler et al. |
| 6,045,996 A | 4/2000 | Cronin et al. |
| 6,090,555 A | 7/2000 | Fiekowsky et al. |
| 6,136,269 A | 10/2000 | Winkler et al. |
| 6,141,096 A | 10/2000 | Stern et al. |
| 6,147,205 A | 11/2000 | McGall et al. |
| 6,159,685 A | 12/2000 | Pinkel et al. |
| 6,177,248 B1 | 1/2001 | Oliner et al. |
| 6,180,349 B1 | 1/2001 | Ginzinger et al. |
| 6,185,030 B1 | 2/2001 | Overbeck |
| 6,188,783 B1 | 2/2001 | Balaban et al. |
| 6,197,506 B1 | 3/2001 | Fodor et al. |
| 6,201,639 B1 | 3/2001 | Overbeck |
| 6,218,803 B1 | 4/2001 | Montagu et al. |
| 6,223,127 B1 | 4/2001 | Berno |
| 6,225,625 B1 | 5/2001 | Pirrung et al. |
| 6,228,575 B1 | 5/2001 | Gingeras et al. |
| 6,261,770 B1 | 7/2001 | Warthoe |
| 6,261,775 B1 | 7/2001 | Bastian et al. |
| 6,262,216 B1 | 7/2001 | McGall |
| 6,265,184 B1 | 7/2001 | Gray et al. |
| 6,268,142 B1 | 7/2001 | Duff et al. |
| 6,269,846 B1 | 8/2001 | Overbeck et al. |
| 6,277,563 B1 | 8/2001 | Shayesteh et al. |
| 6,280,929 B1 | 8/2001 | Gray et al. |
| 6,284,460 B1 | 9/2001 | Fodor et al. |
| 6,300,063 B1 | 10/2001 | Lipshutz et al. |
| 6,300,078 B1 | 10/2001 | Friend et al. |
| 6,303,297 B1 | 10/2001 | Lincoln et al. |
| 6,309,822 B1 | 10/2001 | Fodor et al. |
| 6,310,189 B1 | 10/2001 | Fodor et al. |
| 6,326,148 B1 | 12/2001 | Pauletti et al. |
| 6,333,179 B1 | 12/2001 | Matsuzaki et al. |
| 6,335,167 B1 | 1/2002 | Pinkel et al. |
| 6,344,316 B1 | 2/2002 | Lockhart et al. |
| 6,358,683 B1 | 3/2002 | Collins |
| 6,361,947 B1 | 3/2002 | Dong et al. |
| 6,365,353 B1 | 4/2002 | Lorch et al. |
| 6,368,799 B1 | 4/2002 | Chee |
| 6,408,308 B1 | 6/2002 | Maslyn et al. |
| 6,428,752 B1 | 8/2002 | Montagu |
| 6,432,648 B1 | 8/2002 | Blumenfeld et al. |
| 6,444,426 B1 | 9/2002 | Short et al. |
| 6,451,529 B1 | 9/2002 | Jensen et al. |
| 6,453,241 B1 | 9/2002 | Bassett, Jr. et al. |
| 6,455,258 B2 | 9/2002 | Bastian et al. |
| 6,455,280 B1 | 9/2002 | Edwards et al. |
| 6,465,180 B1 | 10/2002 | Bastian et al. |
| 6,465,182 B1 | 10/2002 | Gray et al. |
| 6,468,744 B1 | 10/2002 | Cronin et al. |
| 6,475,732 B1 | 11/2002 | Shayesteh et al. |
| 6,500,612 B1 | 12/2002 | Gray et al. |
| 6,562,565 B1 | 5/2003 | Pinkel et al. |
| 6,584,410 B2 | 6/2003 | Berno |
| 6,596,479 B1 | 7/2003 | Gray et al. |
| 6,617,137 B2 | 9/2003 | Dean et al. |
| 6,664,057 B2 | 12/2003 | Albertson et al. |
| 6,839,635 B2 | 1/2005 | Bassett, Jr. et al. |
| 6,841,375 B2 | 1/2005 | Su et al. |
| 6,850,846 B2 | 2/2005 | Wang et al. |
| 6,872,529 B2 | 3/2005 | Su |
| 6,879,981 B2 | 4/2005 | Rothschild et al. |
| 6,988,040 B2 | 1/2006 | Mei et al. |
| 7,031,846 B2 | 4/2006 | Kaushikkar et al. |
| 7,197,400 B2 | 3/2007 | Liu et al. |
| 7,280,922 B2 | 10/2007 | Mei et al. |
| 7,424,368 B2 | 9/2008 | Huang et al. |
| 7,629,164 B2 | 12/2009 | Matsuzaki et al. |
| 7,634,363 B2 | 12/2009 | Huang et al. |
| 7,822,555 B2 | 10/2010 | Huang et al. |
| 2002/0029113 A1 | 3/2002 | Wang et al. |
| 2002/0059326 A1 | 5/2002 | Bernhart et al. |
| 2002/0165345 A1 | 11/2002 | Cohen et al. |
| 2002/0168651 A1 | 11/2002 | Cawley et al. |
| 2002/0194201 A1 | 12/2002 | Wilbanks et al. |
| 2003/0096243 A1 | 5/2003 | Busa |
| 2003/0120431 A1 | 6/2003 | Williams et al. |
| 2003/0143614 A1 | 7/2003 | Drmanac |
| 2004/0024537 A1 | 2/2004 | Berno |
| 2004/0117127 A1 | 6/2004 | Cheng |
| 2004/0117128 A1 | 6/2004 | Cheng |
| 2004/0137473 A1 | 7/2004 | Wigler et al. |
| 2004/0138821 A1 | 7/2004 | Chiles et al. |
| 2005/0064476 A1 | 3/2005 | Huang et al. |
| 2005/0123971 A1 | 6/2005 | Di et al. |
| 2005/0130217 A1 | 6/2005 | Huang et al. |
| 2005/0164270 A1 | 7/2005 | Balaban et al. |
| 2005/0208555 A1 | 9/2005 | Raimond, III et al. |
| 2005/0222777 A1 | 10/2005 | Kaushikkar |
| 2005/0244883 A1 | 11/2005 | Williams et al. |
| 2005/0287575 A1 | 12/2005 | Di et al. |
| 2006/0100791 A1 | 5/2006 | Cheng |
| 2006/0167636 A1 | 7/2006 | Kaushikkar et al. |
| 2010/0144542 A1 | 6/2010 | Huang et al. |

FOREIGN PATENT DOCUMENTS

| | | |
|---|---|---|
| WO | 97/10365 A1 | 3/1997 |
| WO | 97/14958 A1 | 4/1997 |
| WO | 97/27317 A1 | 7/1997 |
| WO | 97/29212 A1 | 8/1997 |
| WO | 99/23256 A1 | 5/1999 |
| WO | 99/36760 A1 | 7/1999 |
| WO | 99/47964 A1 | 9/1999 |
| WO | 00/58516 A2 | 10/2000 |
| WO | 01/21839 A2 | 3/2001 |
| WO | 01/58593 A1 | 8/2001 |
| WO | 02/095659 A2 | 11/2002 |
| WO | 2004/058945 A2 | 7/2004 |

OTHER PUBLICATIONS

Zhu et al., "Bayesian Adaptive Sequence Alignment Algorithms," Bioinformatics, 1998, vol. 14, No. 1, pp. 25-39.

Carvalho et al., "Exploration, normalization, and genotype calls of high-density oligonucleotide SNP array data," Biostatistics, 2007, vol. 8, Issue 2, pp. 485-499.

U.S. Appl. No. 09/536,841, filed Mar. 27, 2000, Fan et al.

"BRLMM: an Improved Genotype Calling Method for the GeneChip Human Mapping 500k Array Set," Affymetrix, Inc., revised Apr. 14, 2006, 18 pages.

"BRLMM-P: a Genotype Calling Method for the SNP 5.0 Array," Affymetrix, Inc., revised Feb. 13, 2007, 16 pages.

Bailey, Jr. et al., "Analysis of EST-Driven Gene Annotation in Human Genomic Sequence," Genome Research, 1998, vol. 8, No. 4, pp. 362-376.

Birney, "Hidden Markov Models in Biological Sequence Analysis," IBM Journal of Research and Development, May 2001, vol. 45, Issue 3-4, pp. 449-454.

Buckley et al., "A Full-coverage, High-resolution Human Chromosome 22 Genomic Microarray for Clinical and Research Applications," Human Molecular Genetics, 2002, vol. 11, No. 25, pp. 3221-3229.

(56) References Cited

OTHER PUBLICATIONS

Di et al., "Dynamic model based algorithms for screening and genotyping over 100k SNPs on oligonucleotide microarrays," Bioinformatics, 2005, vol. 21, Issue 9, pp. 1958-1963.
Draghici, "Statistical intelligence: effective analysis of high-density microarray data," Drug Discovery Today, 2002, vol. 7, No. 11, pp. S55-S63.
Dremlyuk, Sel'skokhozyaistvennaya Biology, 6: 119-124 (1984).
Dumar et al., "Genome-wide detection of LOH in prostate cancer using human SNP microarray technology," Genomics, 2003, vol. 81, Issue 3, pp. 260-269.
Ermolaeva et al., "Data management and analysis for gene expression arrays," Nature Genetics, Sep. 1998, vol. 20, pp. 19-23.
Fan et al., "Highly Parallel SNP Genotyping," Cold Spring Harbor Symposia on Quantitative Biology, 2003, vol. 68, pp. 69-78.
Fan et al., "Parallel Genotyping of Human SNPs Using Generic High-Density Oligonucleotide Tag Arrays," Genome Research, 2000, vol. 10, pp. 853-860.
Gingeras et al., "Simultaneous Genotyping and Species Identification Using Hybridization Pattern Recognition Analysis of Generic *Mycobacterium* DNA Arrays," Genome Research, 1998, vol. 8, pp. 435-448.
Gunderson et al., "A genome-wide scalable SNP genotyping assay using microarray technology," Nature Genetics, 2005, vol. 37, No. 5, pp. 549-554.
Halushka et al., "Patterns of Single-Nucleotide Polymorphisms in Candidate Genes for Blood-Pressure Homeostasis," Nature Genetics, 1999, vol. 22, pp. 239-247.
Hardenbol et al, "Multiplexed genotyping with sequence-tagged molecular inversion probes," Nature Biotechnology, 2003, vol. 21, No. 6, pp. 673-678.
Hua et al., "SNiPer-HD: Improved Genotype Calling Accuracy by an Expectation-Maximization Algorithm for High-Density SNP Arrays," Bioinformatics, 2006, vol. 23, Issue 1, 7 pages.
Huang et al., "Whole genome DNA copy number changes identified by high density oligonucleotide arrays," Human Genomics, May 2004, vol. 1, No. 4, pp. 287-299.
Kallioniemi et al., "Comparative Genomic Hybridization for Molecular Cytogenetic Analysis of Solid Tumors," Science, 1992, vol. 258, No. 5083, pp. 818-821.
Kaminski et al., "Practical Approaches to Analyzing Results of Microarray Experiments," American Journal of Respiratory Cell and Molecular Biology, Aug. 2002, vol. 27, pp. 125-132.
Kennedy et al., "Large-scale Genotyping of Complex DNA," Nature Biotechnology, Oct. 2003, vol. 21, No. 10, pp. 1233-1237.
Klein et al., "Comparative Genomic Hybridization, Loss of Heterozygosity, and DNA Sequence Analysis of Single Cells," Proceedings of the National Academy of Sciences, 1999, vol. 96, No. 8, pp. 4494-4499.
Laan et al., "Solid-phase minisequencing confirmed by FISH analysis in determination of gene copy number," Human Genetics, 1995, vol. 96, No. 3, pp. 275-280.
Lindblad-Toh et al., "Loss-of-Heterozygosity Analysis of Small-Cell Lung Carcinomas Using Single-Nucleotide Polymorphism Arrays," Nature Biotechnology, 2000, vol. 18, pp. 1001-1005.
Lipshutz et al., "Using Oligonucleotide Probe Arrays to Access Genetic Diversity," BioTechniques, 1995, vol. 19, No. 3, pp. 442-447.
Lockhart et al., "Expression monitoring by hybridization to high-density oligonucleotide arrays," Nature Biotechnology, Dec. 1996, vol. 14, pp. 1675-1680.
Lovmar et al., "Quantitative evaluation by minisequencing and microarrays reveals accurate multiplexed SNP genotyping of whole genome amplified DNA," Nucleic Acids Research, 2003, vol. 31, No. 21, e129, pp. 1-9.
Lucito et al., "Detecting Gene Copy Number Fluctuations in Tumor Cells by Microarray Analysis of Genomic Representations," Genome Research, 2000, vol. 10, No. 11, pp. 1726-1736.
Lucito et al., "Genetic Analysis Using Genomic Representations," Proceedings of the National Academy of Sciences, 1998, vol. 95, pp. 4487-4492.
Lucito et al., "Representational Oligonucleotide Microarray Analysis: A High-Resolution Method to Detect Genome Copy Number Variations," Genome Research, 2003, vol. 13, No. 10, pp. 2291-2305.
Ma et al., "Biological Data Mining Using Bayesian Neural Networks: A Case Study," International Journal on Artificial Intelligence Tools, 1999, vol. 8, No. 4, pp. 433-451.
Mei et al., "Genome-Wide Detection of Allelic Imbalance Using Human SNPs and High-Density DNA Arrays," Genome Research, 2000, vol. 10, No. 8, pp. 1126-1137.
Michaels et al., "Cluster analysis and data visualization of large-scale gene expression data," Proceedings of the Pacific Symposium on Biocomputing, 1998, vol. 3, pp. 42-53.
Mohapatra et al., "Analyses of Brain Tumor Cell Lines Confirm a Simple Model of Relationships Among Fluorescence In Situ Hybridization, DNA Index, and Comparative Genomic Hybridization," Genes Chromosomes and Cancer, 1997, vol. 20, Issue 4, pp. 311-319.
Mumm et al., "A Classification of 148 U.S. Maize Inbreds: I. Cluster Analysis Based on RFLPs," Crop Science, 1993, vol. 34, No. 4, pp. 842-851.
Paez et al., "Genome coverage and sequence fidelity of ¢29 polymerase-based multiple strand displacement whole genome amplification," Nucleic Acids Research, 2004, vol. 32, No. 9, e71, pp. 1-11.
Palmer, "Ordination Methods for Ecologist, A Glossary of Ordination-Related Terms," Oklahoma State University, Botany Department, http://www.okstate.edu/artsci/botany/ordinate/glossary.htm (Feb. 1998).
Pastinen et al., "A System for Specific, High-throughput Genotyping by Allele-specific Primer Extension on Microarrays," Genome Research, 2000, vol. 10, No. 7, pp. 1031-1042.
Pinkel et al., "High-Resolution Analysis of DNA Copy Number Variation Using Comparative Genomic Hybridization to Microarrays," Nature Genetics, 1998, vol. 20, pp. 207-211.
Pollack et al., "Microarray Analysis Reveals a Major Direct Role of DNA Copy Number Alterations in the Transcriptional Program of Human Breast Tumors," Proceedings of the National Academy of Sciences, Oct. 2002, vol. 99, No. 20, pp. 12963-12968.
Rabbee et al., "A genotype calling algorithm for aftymetrix SNP arrays," Bioinformatics, 2006, vol. 22, No. 1, pp. 7-12.
Schena et al., "Parallel human genome analysis: Microarray-based expression monitoring of 1000 genes," Proceedings of the National Academy of Sciences, Oct. 1996, vol. 93, pp. 10614-10619.
Schena, "Genome analysis with gene expression microarrays," BioEssays, 1996, vol. 18, No. 5, pp. 427-431.
Schubert et al., "Single Nucleotide Polymorphism Array Analysis of Flow-Sorted Epithelial Cells from Frozen Versus Fixed Tissues for Whole Genome Analysis of Allelic Loss in Breast Cancer," American Journal of Pathology, 2002, vol. 160, No. 1, pp. 73-79.
Sebat et al., "Large-Scale Copy Number Polymorphism in the Human Genome," Science, 2004, vol. 305, pp. 525-528.
Sharma et al., "Genetic Divergence and Population Differentiation in Vigna Sublobata (Roxb) Babu and Sharma (Leguminosae-Papilionoideae) and its Cultigens," Current Science, 1986, vol. 55, No. 9, pp. 453-457.
Snijders et al., "Assembly of Microarrays for Genome-wide Measurement of DNA Copy Number," Nature Genetics, 2001, vol. 29, pp. 263-264.
Syvanen, "Toward genome-wide SNP genotyping," Nature Genetics, 2005, vol. 37, pp. S5-S10.
Tatineni et al., "Genetic Diversity in Elite Cotton Germplasm Determined by Morphological Characteristics and RAPDs," Crop Science, 1995, vol. 36, No. 1, pp. 186-192.
Viola, "Complex Feature Recognition: A Bayesian Approach For Learning to Recognize Objects," MIT Artificial Intelligence Laboratory, Nov. 1996, A.I. Memo No. 1591, pp. 1-21.

SYSTEM, METHOD, AND COMPUTER SOFTWARE PRODUCT FOR GENOTYPE DETERMINATION USING PROBE ARRAY DATA

RELATED APPLICATIONS

This application is a divisional of U.S. application Ser. No. 13/468,604 filed on May 10, 2012 which is a continuation of Ser. No. 12/123,463 filed on May 19, 2008, now U.S. Pat. No. 8,200,440 which claims priority to U.S. Provisional Application No. 60/938,757, filed May 18, 2007. The disclosures of each of these applications are hereby incorporated herein by reference in their entirety for all purposes.

BACKGROUND

Field of the Invention

The present invention relates to systems and methods for processing data using information gained from examining biological material. In particular, a preferred embodiment of the invention relates to analysis of processed image data from scanned biological probe arrays for the purpose of determining genotype information via identification of Single Nucleotide Polymorphisms (referred to as SNPs).

Related Art

Synthesized nucleic acid probe arrays, such as Affymetrix GENECHIP® probe arrays, and spotted probe arrays, have been used to generate unprecedented amounts of information about biological systems. For example, the GENECHIP® Mapping 500K Array Set available from Affymetrix, Inc. of Santa Clara, Calif., is comprised of two microarrays capable of genotyping on average 250,000 SNPs per array. Newer arrays developed by Affymetrix can contain probes sufficient to genotype up to one million SNPs per array. Analysis of genotype data from such microarrays may lead to the development of new drugs and new diagnostic tools.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials made by spotting or other methods such as photolithography or bead based systems. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GENECHIP® arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

An embodiment of a method of analyzing data from processed images of biological probe arrays is described that comprises receiving a plurality of files comprising a plurality of intensity values associated with a probe on a biological probe array; normalizing the intensity values in each of the data files; determining an initial assignment for a plurality of genotypes using one or more of the intensity values from each file for each assignment; estimating a distribution of cluster centers using the plurality of initial assignments; combining the normalized intensity values with the cluster centers to determine a posterior estimate for each cluster center; and assigning a plurality of genotype calls using a distance of the one or more intensity values from the posterior estimate.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 160 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION

Figure 1:
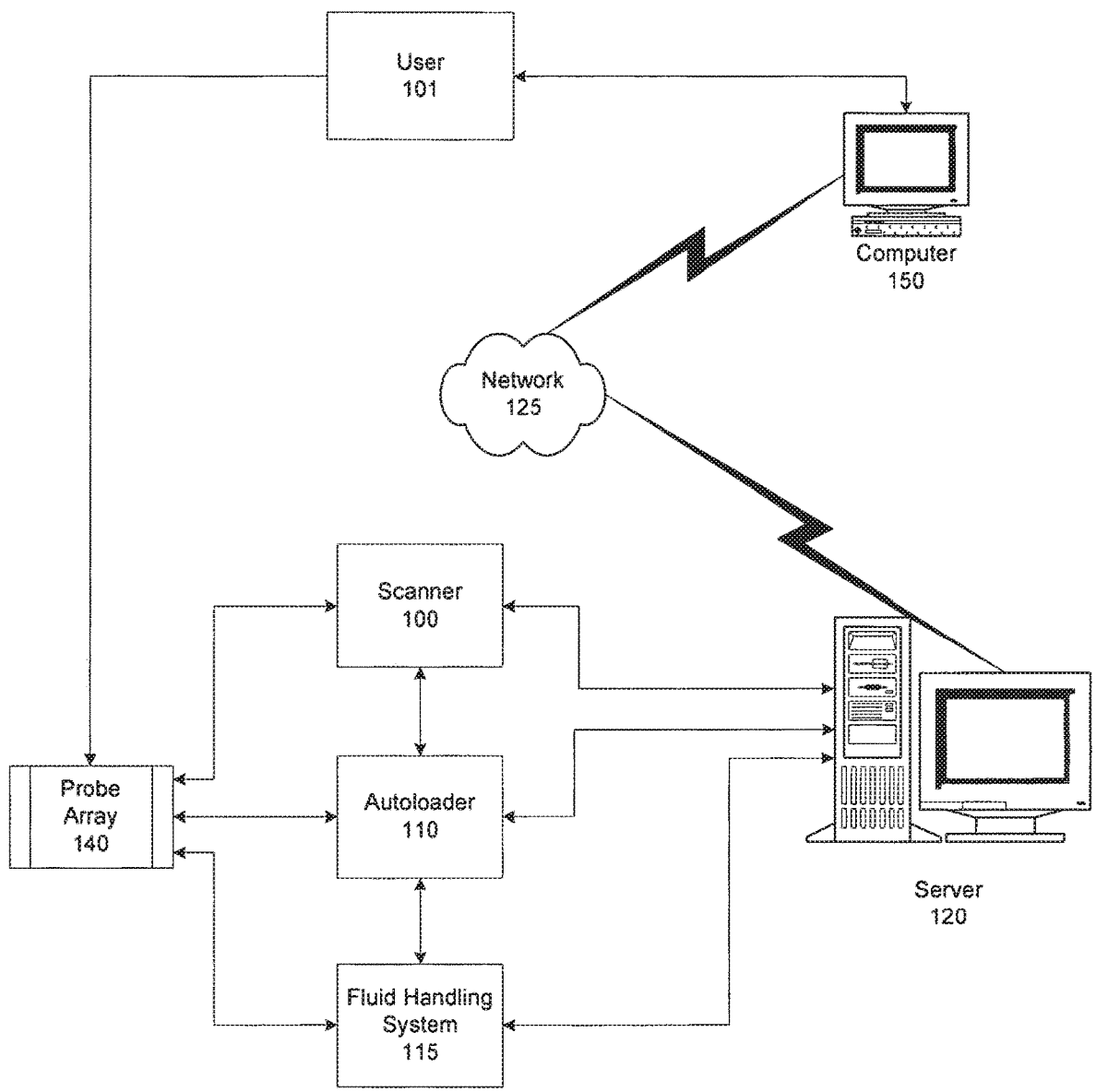
FIG. 1 is a functional block diagram of one embodiment of a computer and a server enabled to communicate over a network, as well as a probe array and probe array instruments.

Highly accurate and reliable genotype calling is an essential component of high-density SNP genotyping technology. Rabbee and Speed recently developed a model called the Robust Linear Model with Mahalanobis distance classifier (RLMM, pronounced 'realm') (See Nusrat Rabbee and Terence P. Speed, "A genotype calling algorithm for Afjymetrix SNP arrays" UC Berkeley Statistics Online Tech Reports, August 2005, hereby incorporated by reference in its entirety). We present here an extension of the RLMM model developed for a commercial nucleic acid array product which improves overall performance (call rates and accuracy) and this extension only requires probes hybridizing to the SNP alleles (the perfect match probes) and does not require use of mis-matched probes, unlike BRLMM, a variation of RLMM that includes a Bayesian step which provides improved estimates of cluster centers and variances. The model disclosed herein is called BRLMM-P. Bayesian probability is an interpretation of probability suggested by Bayesian theory, which holds that the concept of probability can be defined as the degree to which a person believes a proposition. Bayesian theory also suggests that Bayes' theorem can be used as a rule to infer or update the degree of belief in light of new information. There are further differences that are disclosed below.

Additionally, one advantage is that RLMM performs a multiple chip analysis, enabling the simultaneous estimation of probe effects and allele signals for each SNP. Accounting for probe specific effects results in lower variance on allele signal estimates. Also, another advantage is the estimation of genotypes by a multiple-sample classification. It integrates information as necessary from existing, known SNPs to better predict the properties of the underlying clusters corresponding to the BB, AB, and AA genotypes. The present algorithm, based on the above RLMM model, makes weaker assumptions about the behavior of probe intensities than does some other algorithms, making it far more robust in the presence of real-world data.

a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term"an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,945,334, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/USOI/04285 (International Publication Number WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays. Nucleic acid arrays that are useful in the present invention include those that are commercially available from Affymetrix (Santa Clara, Calif.) under the brand name GENECHIP®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. PGPub Nos. 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual ($2^{nd}$ Ed. Cold Spring Harbor, N.Y, 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389, 194, 10/913,102, 10/846,261, 11/260,617 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), Ser. Nos. 10/065,856, 10/065, 868, 10/328,818, 10/328,872, 10/423,403, and 60/482,389.

b) Definitions

The term "admixture" refers to the phenomenon of gene flow between populations resulting from migration. Admixture can create linkage disequilibrium (LD).

The term "allele" as used herein is any one of a number of alternative forms a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM IVIES, 1 M [Na+], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GENECHIP® Mapping Assay Manual, 2004.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., Nat. Rev. Gen. 3:299-309, 2002.

The term "lod score" or "LOD" is the log of the odds ratio of the probability of the data occurring under the specific hypothesis relative to the null hypothesis. LOD=log [probability assuming linkage/probability assuming no linkage].

The terms "mismatch" and "perfect match" describe the relationship between the sequence of the intended target and the probe that is on an array. A perfect match probe is designed to exactly match the intended target sequence. The mismatch is designed to have at least one base that is not part of the intended target. A mismatch probe is a probe that is designed to be complementary to a reference sequence except for some mismatches that may significantly affect the hybridization between the probe and its target sequence. In preferred embodiments, mismatch probes are designed to be complementary to a reference sequence except for a homomeric base mismatch at the central (e.g., 13th in a 25 base probe) position. Mismatch probes are normally used as controls for cross-hybridization. A probe pair is usually composed of a perfect match and its corresponding mismatch probe. In preferred embodiments, the difference between perfect match and mismatch provides an intensity difference in a probe pair. The array that is preferred in the present invention contains all perfect match probes and does not include mismatch probes for target sequences.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, mini satellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "prior" as used as a noun herein refers to an estimate of a parameter plus the uncertainty in the distribution of that parameter that is entered into the calculation before any (current) data is observed. This is standard notation in Bayesian statistics. Such values as estimates for genotype cluster center locations and variances can be used as prior values (such as ones obtained from other data sets or user entered quantities).

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies. The array that is preferred in the present invention contains all perfect match probes and does not include mismatch probes for target sequences.

c) Embodiments of the Present Invention

Embodiments of an image analysis system comprising an image analysis and instrument control application are described herein that provide a flexible and dynamically configurable architecture and a low level of complexity. In particular, embodiments are described that provide file management functionality where each file comprises a unique identifier and logical relationships between the files using those identifiers. Further, the embodiments include a modular architecture for customizing components and functionality to meet individual needs as well as user interfaces provided over a network that provide a less restrictive workflow environment.

Probe Array 140: An illustrative example of probe array 140 is provided in FIGS. 1, 2, and 3. Descriptions of probe arrays are provided above with respect to "Nucleic Acid Probe arrays" and other related disclosure. In various implementations, probe array 140 may be disposed in a cartridge or housing. Examples of probe arrays and associated cartridges or housings may be found in U.S. Pat. Nos. 5,945,334, 6,287,850, 6,399,365, 6,551,817, each of which is also hereby incorporated by reference herein in its entirety for all purposes. In addition, some embodiments of probe array 140 may be associated with pegs or posts, where for instance probe array 140 may be affixed via gluing, welding, or other means known in the related art to the peg or post that may be operatively coupled to a tray, strip or other type of similar substrate. Examples with embodiments of probe array 140 associated with pegs or posts may be found in U.S. patent Ser. No. 10/826,577.

Scanner 100: Labeled targets hybridized to probe arrays may be detected using various devices, sometimes referred to as scanners, as described above with respect to methods and apparatus for signal detection.

An illustrative device is shown in FIG. 1 as scanner 100. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 µm, 1.5 µm, 1.0 µm, or sub-micron pixel size. Two examples where the signal may be incorporated into data are data files in the form *.dat or *.tif as generated respectively by Affymetrix Microarray Suite (described in U.S. Pat. No. 7,031,846) based on images scanned from GENECHIP® arrays. Examples of scanner systems that may be implemented with embodiments of the present invention include U.S. patent application Ser. No. 10/389,194 now U.S. Pat. No. 7,689,022, Ser. No. 10/846,261 now U.S. Pat. No. 7,148,492, Ser. No. 10/913,102 now U.S. Pat. No. 7,317,415, and Ser. No. 11/260,617 now U.S. Pat. No. 7,682,782, each of which are incorporated by reference above.

Autoloader 110: Illustrated in FIG. 1 is autoloader 110 that is an example of one possible embodiment of an automatic loader that provides transport of one or more probe arrays 140 used in conjunction with scanner 100 and fluid handling system 115.

In some embodiments, autoloader 110 may include a number of components such as, for instance, a magazine, tray, carousel, or other means of holding and/or storing a plurality of probe arrays; a transport assembly; and a thermal control chamber. For example, some implementations of autoloader 110 may include features for preserving the biological integrity of the probe arrays for extended periods such as, for instance, a period of up to sixteen hours. Also in the present example, in the event of a power failure or error condition that prevents scanning or other processing steps, autoloader 110 will indicate the failure to user 101 and maintain storage temperature for all probe arrays 140 through the use of what may be referred to as an uninterruptable power supply system. The power failure or other error may be communicated to user 101 by one or more methods that could include audible/visual alarm indicators, a graphical user interface, automated paging system, alert via a graphical user interface provided by instrument control and image analysis applications 372, or other means of automated communication. Still continuing with the present example, the power supply system could also support one or more other systems such as scanner 100 or fluid handling system 115.

Some embodiments of autoloader 110 may include preheating each embodiment of probe array 140 to a preferred temperature prior to or during particular processing or image acquisition operations. For example, autoloader 110 may employ a thermally controlled chamber to pre-heat one or more probe arrays 140 to the same temperature as the internal environment of scanner 100 prior to transport to the scanner. Similarly, autoloader 110 could bring probe array 140 to the appropriate hybridization temperature prior to loading into fluid handling system 115. Also in the present example, autoloader 110 may also employ one or more thermal control operations as post-processing steps such as when autoloader 110 removes each of probe arrays 140 from scanner 100, autoloader 110 may employ one or more environmental or temperature control elements to warm or cool the probe array to a preferred temperature in order to preserve biological integrity.

Many embodiments of autoloader 110 are enabled to provide automated loading/unloading of probe arrays 140 to both fluid handling system 115 and/or scanner 100. Also, some embodiments of autoloader 110 may be equipped with a barcode reader, or other means of identification and information storage such as, for instance, magnetic strips, what are referred to by those of ordinary skill in the related art as radio frequency identification (RFID), or one or more microchips associated with each embodiment of probe array 140. For example, autoloader 110 may read or otherwise identify encoded information from the means of identification and information storage that in the present example may include a barcode associated with probe array 140. Autoloader 110 may use the information and/or identifier directly in one or more operations or alternatively may forward the information and/or identifier to instrument control and image analysis applications 372 of server 120 for processing, where applications 372 may then provide instruction to autoloader 110 based, at least in part, upon the processed information and/or identifier. Also in some implementations, scanner 100 and/or fluid handling system 115 may also be similarly equipped with a barcode reader or other means as described above.

Additional examples of autoloaders and probe array storage instruments are described in U.S. patent application Ser. Nos. 10/389,194 and 10/684,160; and U.S. Pat. Nos. 6,511,277 and 6,604,902 each of which is hereby incorporated herein by reference in their entireties for all purposes.

Fluid Handling System 115: Embodiments of fluid handling system 115, as illustrated in FIG. 1, may implement one or more procedures or operations for hybridizing one or more experimental samples to probes associated with one or more probe arrays 140, as well as operations that, for instance, may include exposing each of probe arrays 140 to washes, buffers, stains, or other fluids in a sequential or parallel fashion. Some embodiments of the present invention may include probe array 140 enclosed in a housing or cartridge that may be placed in a carousel, tray, or other means of holding for transport or processing as previously described with respect to autoloader 110. For example, a carousel, tray, or carrier may be specifically enabled to register a plurality of probe array 140/housing embodiments in a specific orientation and may enable or improve high throughput processing of each of the plurality of probe arrays 140 by providing positive positional registration so that the robotic instrument may carry out processing steps in an efficient and repeatable fashion. Additional examples of a fluid handling system that interacts with various implementations of probe array 140/housing embodiments is described in U.S. patent application Ser. No. 11/057,320, which is hereby incorporated by reference herein in its entirety for all purposes.

Embodiments of fluid handling system 115 could include a plurality of elements enabled to automatically introduce and remove fluids from a probe array 140 without user intervention such as, for instance, one or more sample holders, fluid transfer devices, and fluid reservoirs. For example, applications 372 may direct fluid handling system 115 to add a specified volume of a particular sample to an associated implementation of probe array 140. In the present example, fluid handling system 115 removes the specified volume of sample from a reservoir positioned in a sample holder via one of sample transfer pins, pipettes or pipette tips, specialized adaptors, or other means known to those of ordinary skill in the related art. In some embodiments, the sample holder may be thermally controlled in order to maintain the integrity of the samples, reagents, or fluids contained in the reservoirs, for a preferred temperature according to a specific protocol or processing step, or for temperature consistency of the various fluids exposed to probe array 140. The term "reservoir" as used herein could include a vial, tube, bottle, 96 or 384 well plate, or some other container suitable for holding volumes of liquid. Also in the present example, fluid handling system 115 may employ a vacuum/pressure source, valves, and means for fluid transport known to those of ordinary skill in the related art.

In some embodiments, fluid handling system 115 may interface with each of one or more of probe arrays 140 by moving a fluid transfer device such as, for instance, what may be referred to as a pin or needle such as a dual lumen needle, pipette tip, specialized adaptor or other type of fluid transfer device known in the art. For example, as those of ordinary skill in the related art will appreciate, a plurality of fluid transfer devices such as a robotic device comprising a pipettor component coupled to one or more pipette tips may be employed to engage with one or more of interfaces or alternatively direct fluid to an exposed surface, in order to process one or more of probe arrays 140, where a plurality of probe arrays 140 may be processed in parallel. In the present example, fluid handling system 115 may simultaneously or in a sequential fashion process a plurality of probe arrays 140 by removing a specified aliquot of sample or other type of fluid from each reservoir disposed in one or more sample holders and deliver each sample or fluid to probe array 140.

Fluid handling system 115 may remove used sample or waste fluids from probe array 140 by, for instance, creating a negative pressure or vacuum through one or more ports associated with a housing. Alternatively, fluids may be similarly expelled using a positive pressure of air, gas, or other type of fluid either alone or in combination with the negative pressure, through one or more ports where the positive pressure may cause the undesired fluid to be expelled through one or more channels or away from an exposed surface. Expelled of removed fluids may be stored in one or more reservoir or alternatively may be expelled from fluid handling system 115 into another waste receptacle or drain. For example, it may be desirable in some implementations for user 101 to recover a sample from probe array 140 and store the recovered sample in an environmentally controlled receptacle in order to preserve the biological integrity.

As those of ordinary skill in the related art will appreciate, the sample content of each reservoir within a sample holder is known so that applications 372 may associate an experimental sample or fluid with a particular embodiment of probe array 140. Fluid handling system 115 may also provide one or more detectors associated with the sample holder to indicate to applications 372 when a reservoir is present or absent. Additionally, fluid handling system 115 may include one or more implementations of a barcode reader, or other means of identification described above with respect to autoloader 110, enabled to identify each reservoir using an associated barcode identifier or other type of machine readable identifier.

Some embodiments of fluid handling system 115 may include one or more detection systems enabled to detect the presence and identity of a fluid associated with probe array 140. Also, some embodiments of fluid handling system 115 may provide an environment that promotes the hybridization of a biological target contained in a sample to the probes of the probe array. Some environmental conditions that affect the hybridization efficiency could include temperature, gas bubbles, agitation, oscillating fluid levels, or other conditions that could promote the hybridization of biological samples to probes. Other environmental conditions that fluid handling system 115 may provide may include a means to provide or improve mixing of fluids. For example a means of shaking probe array 140 to promote inertial movement of fluids and turbulent flow may include what is generally referred as a plate shaker, rotating carousel, or other shaking instrument. Other sources of fluid mixing could be provided by an ultrasonic source or mechanical source such as for instance a piezo-electric agitation source, or other means of providing mechanical agitation. In the present example, the agitation or shaking means may provide fluidic movement that may improve the efficiency of hybridization of target molecules in a sample to probe array 140. Other examples of elements and methods for mixing fluids in a chamber are provided in U.S. patent application Ser. No. 11/017,095, titled "System and Method for Improved Hybridization Using Embedded Resonant Mixing Elements", filed Dec. 20, 2004 which is hereby incorporated by reference herein in its entirety for all purposes.

Embodiments of fluid handling system 115 may also perform what those of ordinary skill in the related art may refer to as post hybridization operations such as, for instance, washes with buffers or reagents, water, labels, or antibodies. For example, staining may include introducing a stain comprising molecules with fluorescent tags that selectively bind to the biological molecules or targets that have hybridized to probe array 140. Additional post-hybridization operations may, for example, include the introduction of what is referred to as a non-stringent buffer to probe array 140 to preserve the integrity of the hybridized array.

Some implementations of fluid handling system 115 allow for interruption of operations to insert or remove probe arrays, samples, reagents, buffers, or any other materials. After interruption, fluid handling system 115 may conduct a scan of some or all identifiers associated with probe arrays, samples, carousels, trays, or magazines, user input identifiers, or other identifiers used in an automated process. For example, user 101 may wish to interrupt the process conducted by fluid handling system 115 to remove a tray of samples and insert a new tray. The interruption is communicated to user 101 by a variety of methods, and the user performs the desired tasks. User 101 inputs a command for the resumption of the process that may begin with fluid handling system 115 scanning all available barcode identifiers. Applications 372 determines what has been changed, and makes the appropriate adjustments to procedures and protocols.

Fluid handling system 115 may also perform operations that do not act directly upon a probe array. Such functions could include the management of fresh versus used reagents and buffers, experimental samples, or other materials utilized in hybridization operations. Additionally, fluid handling system 115 may include features for leak control and isolation from systems that may be sensitive to exposure to liquids. For example, a user may load a variety of experimental samples into fluid handling system 115 that have unique experimental requirements. In the present example the samples may have barcode labels with unique identifiers associated with them. The barcode labels could be scanned with a hand held reader or alternatively fluid handling system 115 could include a dedicated reader. Alternatively, other means of identification could be used as described above. The user may associate the identifier with the sample and store the data into one or more data files. The sample may also be associated with a specific probe array type that is similarly stored.

Additional examples of hybridization and other type of probe array processing instruments are described in U.S. patent application Ser. Nos. 10/684,160 and 10/712,860, both of which are hereby incorporated by reference herein in their entireties for all purposes.

Computer 150: An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input-output devices 240, and display devices 245. Display devices 245 may include display devices that provides visual information, this information typically may be logically and/or physically organized as an array of pixels. A Graphical user interface (GUI) controller may also be included that may comprise any of a variety of known or future software programs for providing graphical input and output interfaces such as for instance GUI's 246. For example, GUI's 246 may provide one or more graphical representations to a user, such as user 101, and also be enabled to process user inputs via GUI's 246 using means of selection or input known to those of ordinary skill in the related art.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor or it may be one of other processors that are or will become available. Some embodiments of processor 255 may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads. In addition, those of ordinary skill in the related will appreciate that processor 255 may be configured in what is generally referred to as 32 or 64 bit architectures, or other architectural configurations now known or that may be developed in the future.

Processor 255 executes operating system 260. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, USB or flash drive, or a diskette drive. Such types of memory storage devices 281 typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
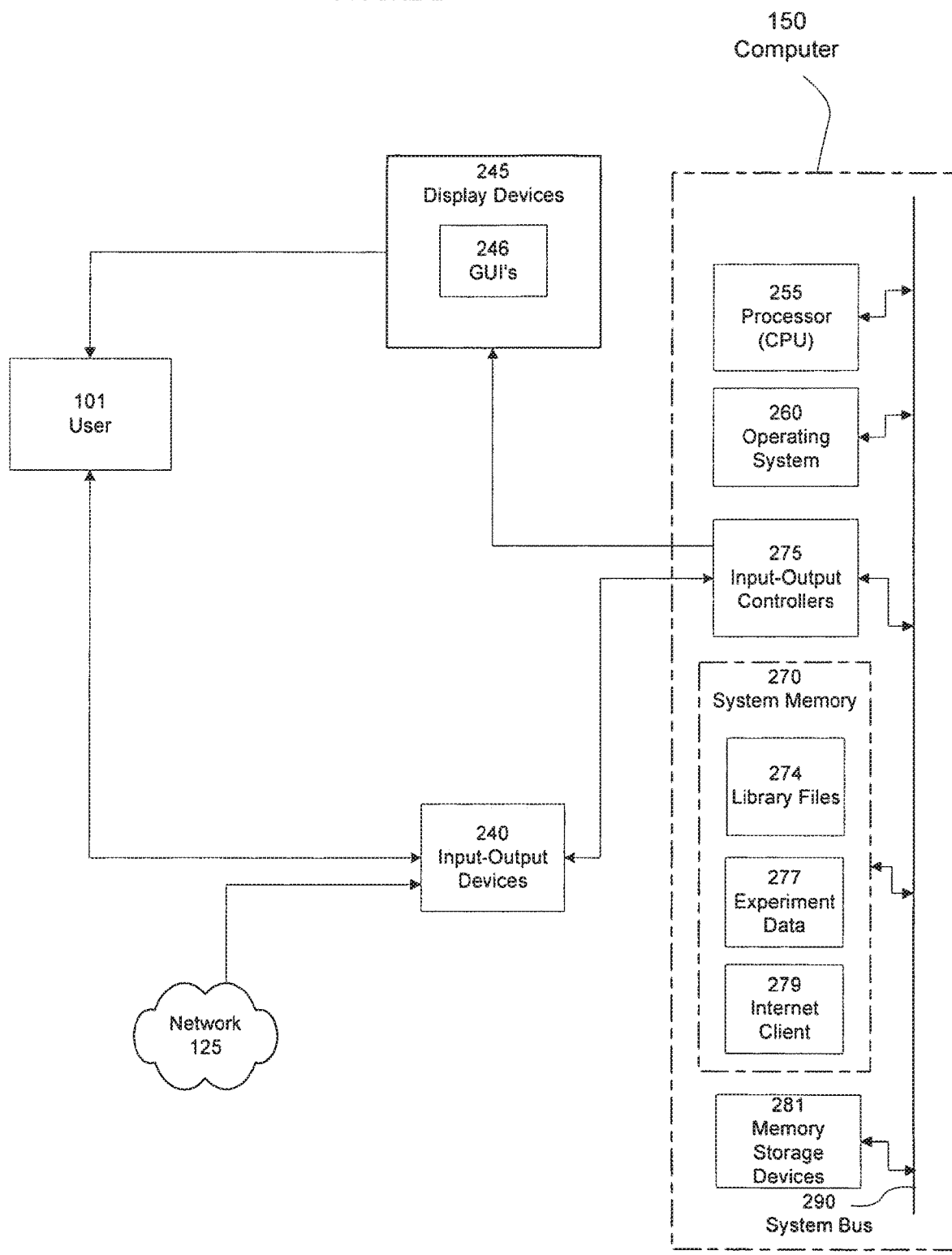
FIG. 2 is a functional block diagram of one embodiment of the computer system of FIG. 1, including a display device that presents a graphical user interface to a user.
Figure 3:
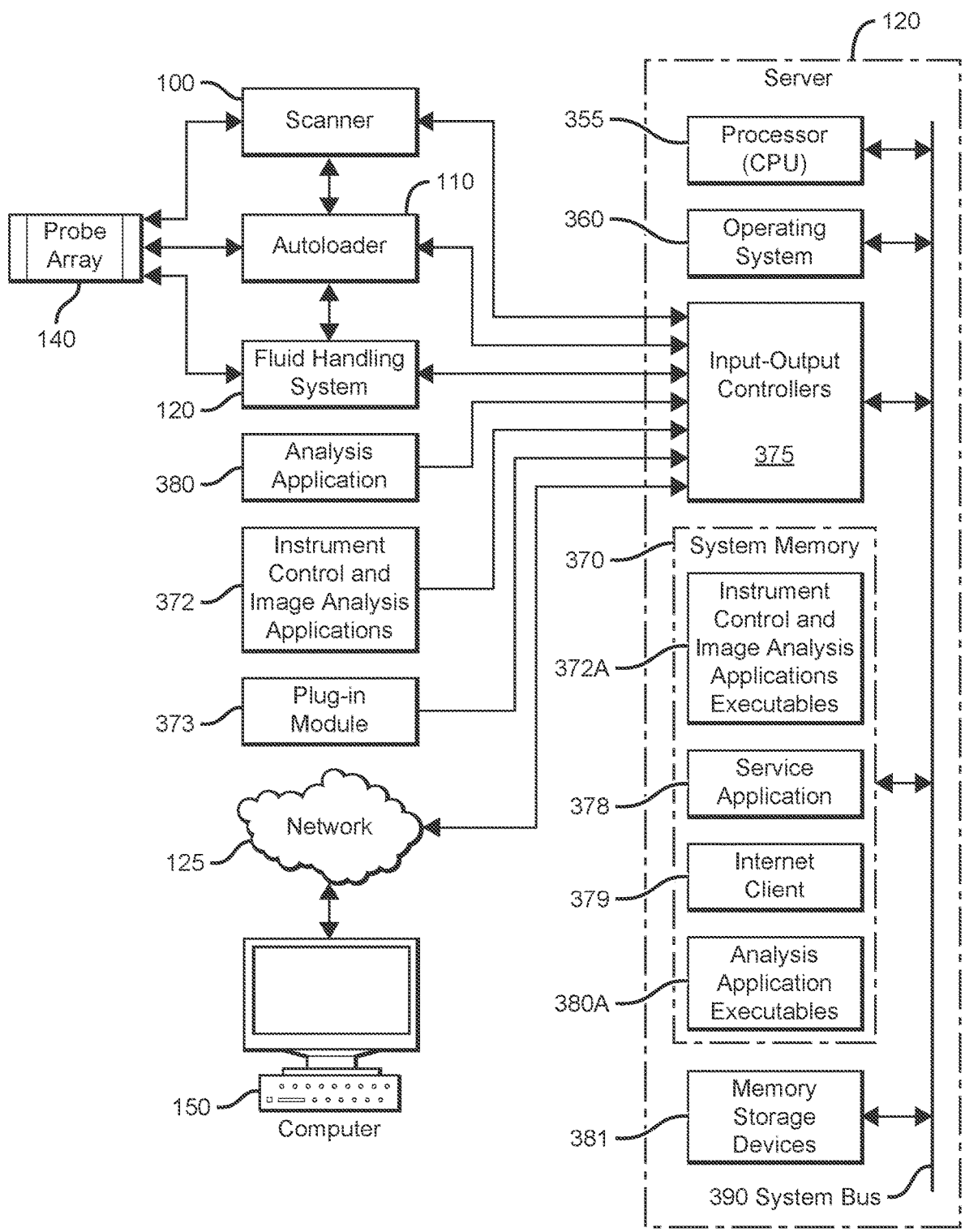
FIG. 3 is a functional block diagram of one embodiment of the server of FIG. 1, where the server comprises an executable instrument control and image analysis application.

As will be evident to those skilled in the relevant art, an instrument control and image processing application, such as for instance an implementation of instrument control and image processing applications 372 illustrated in FIG. 3, if implemented in software, may be loaded into and executed from system memory 270 and/or memory storage device 281. All or portions of the instrument control and image processing applications may also reside in a read-only memory or similar device of memory storage device 281, such devices not requiring that the instrument control and image processing applications first be loaded through input-output controllers 275. It will be understood by those skilled in the relevant art that the instrument control and image processing applications, or portions of it, may be loaded by processor 255 in a known manner into system memory 270, or cache memory (not shown), or both, as advantageous for execution. Also illustrated in FIG. 2 are library files 274, experiment data 277, and internet client 279 stored in system memory 270. For example, experiment data 277 could include data related to one or more experiments or assays such as excitation wavelength ranges, emission wavelength ranges, extinction coefficients and/or associated excitation power level values, or other values associated with one or more fluorescent labels. Additionally, internet client 279 may include an application enabled to accesses a remote service on another computer using a network that may for instance comprise what are generally referred to as "Web Browsers". Also, in the same or other embodiments internet client 279 may include, or could be an element of, specialized software applications enabled to access remote information via a network such as network 125 such as, for instance, the GENECHIP® Data Analysis Software (GDAS) package or Chromosome Copy Number Tool (CNAT) both available from Affymetrix, Inc. of Santa Clara Calif. that are each enabled to access information from remote sources, and in particular probe array annotation information from the NETAFFX® web site hosted on one or more servers provided by Affymetrix, Inc.

Network 125 may include one or more of the many various types of networks well known to those of ordinary skill in the art. For example, network 125 may include a local or wide area network that employs what is commonly referred to as a TCP/IP protocol suite to communicate, that may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Server 120: FIG. 1 shows a typical configuration of a server computer connected to a workstation computer via a network that is illustrated in further detail in FIG. 3. In some implementations any function ascribed to Server 120 may be carried out by one or more other computers, and/or the functions may be performed in parallel by a group of computers.

Typically, server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as processor 355, operating system 360, system memory 370, memory storage devices 381, and input-output controllers 378. It will be understood by those skilled in the relevant art that there are many possible configurations of the components of server 120 that may typically include cache memory, a data backup unit, and many other devices. Similarly, many hardware and associated software or firmware components may be implemented in a network server. For example, components to implement one or more firewalls to protect data and applications, uninterruptable power supplies, LAN switches, web-server routing software, and many other components. Those of ordinary skill in the art will readily appreciate how these and other conventional components may be implemented.

Processor 355 may include multiple processors. Processor 355 executes operating system 360. Some embodiments of processor 355 may also include what are referred to as Multi-core processors and/or be enabled to employ parallel processing technology in a single or multi-core configuration similar to that as described above with respect to processor 255. In addition, those of ordinary skill in the related will appreciate that processor 355 may be configured in what is generally referred to as 32 or 64 bit architectures, or other architectural configurations now known or that may be developed in the future.

Operating system 360 interfaces with firmware and hardware in a well-known manner, and facilitates processor 355 in coordinating and executing the functions of various computer programs that may be written in a variety of programming languages. Operating system 360, typically in cooperation with the processor, coordinates and executes functions of the other components of server 120. Operating system 360 also provides scheduling, input-output control, file and data management, memory management, and communication control and related services, all in accordance with known techniques.

System memory 370 may be any of a variety of known or future memory storage devices. Examples include any commonly available random access memory (RAM), magnetic medium such as a resident hard disk or tape, an optical medium such as a read and write compact disc, or other memory storage device. Memory storage device 381 may be any of a variety of known or future devices, including a compact disk drive, a tape drive, a removable hard disk drive, USB or flash drive, or a diskette drive. Such types of memory storage device typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in the system memory and/or the program storage device used in conjunction with the memory storage device.

In some embodiments, a computer program product is described comprising a computer usable medium having control logic (computer software program, including program code) stored therein. The control logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 375 could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via system bus 390. Some of these communications may be accomplished in alternative embodiments using network or other types of remote communications.

As will be evident to those skilled in the relevant art, a server application if implemented in software, may be loaded into the system memory and/or the memory storage device through one of the input devices, such as instrument control and image processing applications 372 described in greater detail below. All or portions of these loaded elements may also reside in a read-only memory or similar device of the memory storage device, such devices not requiring that the elements first be loaded through the input devices. It will be understood by those skilled in the relevant art that any of the loaded elements, or portions of them, may be loaded by the processor in a known manner into the system memory, or cache memory (not shown), or both, as advantageous for execution.

Instrument control and image processing applications 372: Instrument control and image processing applications 372 may comprise any of a variety of known or future image processing applications. Some examples of known instrument control and image processing applications include the Affymetrix Microarray Suite, and Affymetrix GENECHIP® Operating Software (hereafter referred to as GCOS) applications. Typically, embodiments of applications 372 may be loaded into system memory 270 and/or memory storage device 281 through one of input devices 240.

Some improved embodiments of applications 372 include executable code being stored in system memory 270, illustrated in FIG. 3 as instrument control and analysis applications executables 372A, of an implementation of server 120. For example, the described embodiments of applications 372 may include what may be referred to as the Affymetrix command-console software. Embodiments of applications 372 may advantageously provide what is referred to as a modular interface for one or more computers or workstations and one or more servers, as well as one or more instruments. The term "modular" as used herein generally refers to elements that may be integrated to and interact with a core element in order to provide a flexible, updateable, and customizable platform. For example, as will be described in greater detail below applications 372 may comprise a "core" software element enabled to communicate and perform primary functions necessary for any instrument control and image processing application. Such primary functionality may include communication over various network architectures. In the present example, modular software elements, such as for instance plug-in module 376, may be interfaced with the core software element to perform more specific or secondary functions. In particular, the specific or secondary functions may include functions customizable for particular applications desired by user 101. Further, modules integrated with the core software elements are considered to be a single software application such as applications 372.

In the presently described implementation, applications 372 may communicate with and control one or more elements or processes of the one or more servers, one or more workstations, and the one or more instruments. Also, embodiments of server 120 or computer 150 with an implementation of applications 372 stored thereon could be located locally or remotely and communicate with one or more additional servers and/or one or more other computers/workstations or instruments.

In some embodiments, applications 372 may also be enabled to encrypt data such as one or more data files that will be described in greater detail below, where the encrypted data may then be distributed over network 125 to one or more other computers or servers. For example, some embodiments of probe array 140 may be employed for diagnostic purposes where the data may be associated with a patient and a diagnosis of a disease or medical condition. It is desirable in many applications to protect the data using encryption for confidentiality of patient information. In addition, one-way encryption technologies may be employed in situations where access should be limited to only selected parties such as a patient and their physician. In the present example, only the selected parties have the key to decrypt or associate the data with the patient. In some applications, the one-way encrypted data may be stored in one or more public databases or repositories where even the curator of the database or repository would be unable to associate the data with the user. The described encryption functionality may also have utility in clinical trial applications where it may be desirable to isolate one or more data elements from each other for the purpose of confidentiality and/or removal of experimental biases.

Applications 372 may, in the present implementation, provide one or more interactive graphical user interfaces that allows user 101 to make selections based upon information presented in an embodiment of GUI 246. Those of ordinary skill will recognize that embodiments of GUI 246 may be coded in various language formats such as an HTML, XHTML, XML, javascript, Jscript, or other language known to those of ordinary skill in the art used for the creation of enhancement of "Web Pages" viewable and compatible with internet client 379. As described above with respect to internet client 279, internet client 379 may include various internet browsers such as Microsoft Internet Explorer, Netscape Navigator, Mozilla Firefox, Apple Safari, or other browsers known in the art. Applications of GUI's 246 viewable via one or more internet type browsers may allow user 101 complete remote access to data, management, and registration functions without any other specialized software elements. Applications 372 may provide one or more implementations of interactive GUI's 246 that allow user 101 to select from a variety of options including data selection, experiment parameters, calibration values, and probe array information within the access to data, management, and registration functions.

In some embodiments, applications 372 may be capable of running on operating systems in a non-English format, where applications 372 can accept input form user 101 in various non-English language formats such as French, Spanish etc., and output information to user 101 in the same or other desired language output. For example, applications 372 may present information to user 101 in various implementations of GUI 246 in a language output desired by user 101, and similarly receive input from user 101 in the desired language. In the present example, applications 372 is internationalized such that it is capable of interpreting the input from user 101 in the desired language where the input is acceptable input with respect to the functions and capabilities of applications 372.

Embodiments of applications 372 also include instrument control features, where the control functions of individual types or specific instruments such as scanner 100, autoloader 110, or fluid handling system 115 may be organized as plug-in type modules to applications 372. For example, each plug-in module may be a separate component such as plug-in module 373 and may provide definition of the instrument control features to applications 372 where each plug-in module 373 is functionally integrated with executables 372A when stored in system memory 370. In the present example, each instrument may have one or more associated embodiments of plug-in module 373 that for instance may be specific to model of instrument, revision of instrument firmware or scripts, number and/or configuration of instrument embodiment, etc. Further, multiple embodiments of plug-in module 373 for the same instrument such as scanner 100 may be stored in system memory 370 for use by applications 372, where user 101 may select the desired embodiment of module 373 to employ, or alternatively such a selection of module 373 may be defined by data encoded directly in a machine readable identifier as described below or indirectly via the array file, library files, experiments files and so on.

The instrument control features may include the control of one or more elements of one or more instruments that could, for instance, include elements of a hybridization device, fluid handling system 115, autoloader 110, and scanner 100. The instrument control features may also be capable of receiving information from the one more instruments that could include experiment or instrument status, process steps, or other relevant information. The instrument control features could, for example, be under the control of or an element of the interface of applications 372. In some embodiments, a user may input desired control commands and/or receive the instrument control information via one of GUI's 246. Additional examples of instrument control via a GUI or other interface is provided in U.S. patent application Ser. No. 10/764,663, which is hereby incorporated by reference herein in its entirety for all purposes.

Figure 4:
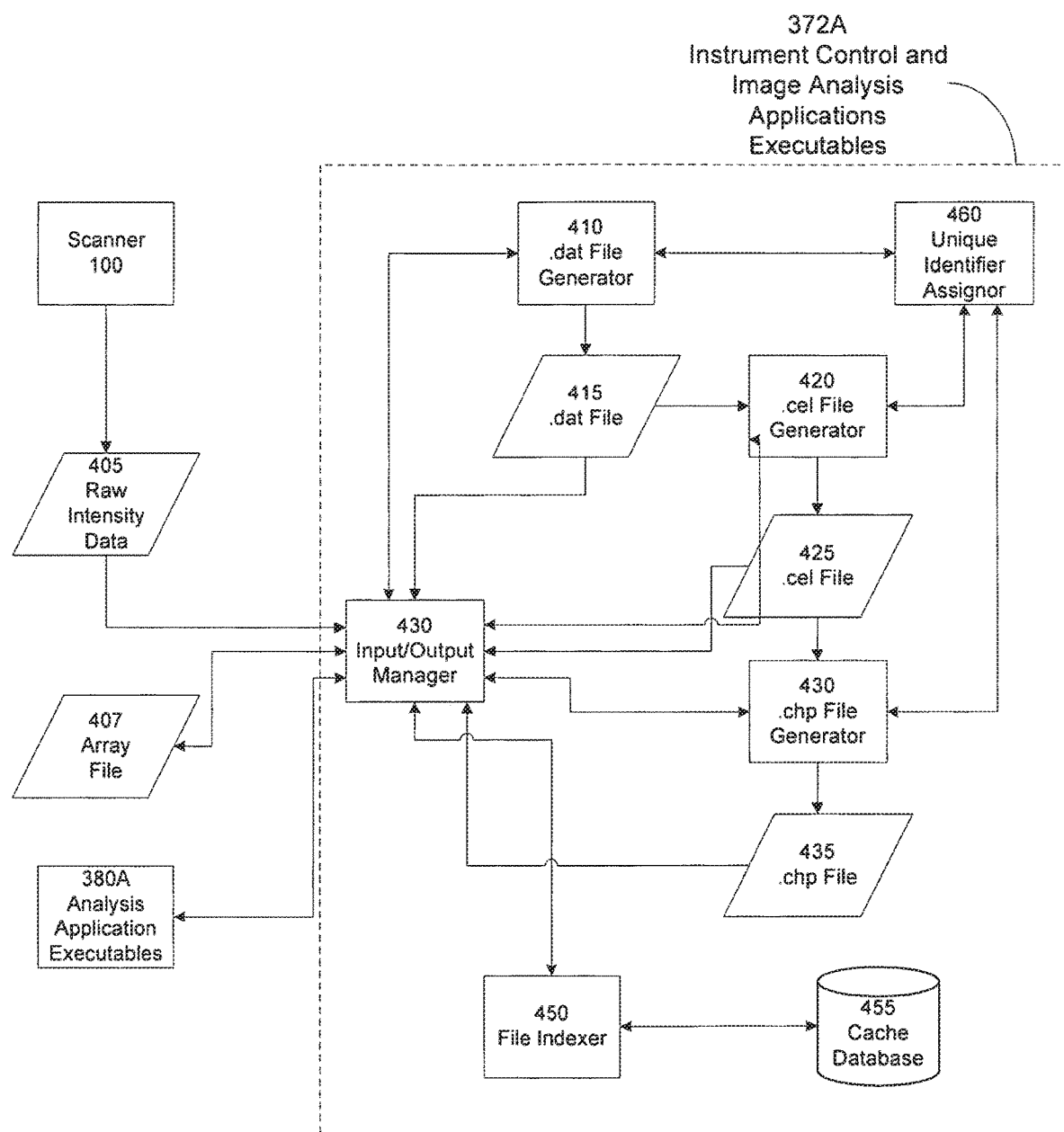
FIG. 4 is a functional block diagram of one embodiment of the instrument control and image analysis application of FIG. 3 comprising an analysis application that receives process image files from the instrument control and image analysis application of FIG. 3 for additional analysis.

In some embodiments, applications 372 may employ what may referred to as an "array file", represented in FIG. 4 as array file 407 that comprises data employed for various processing functions of images by applications 372 as well as other relevant information. Generally it is desirable to consolidate elements of data or metadata related to an embodiment of probe array 140, experiment, user, or some combination thereof, to a single file that is not duplicated (i.e. as embodiments of .dat file 415 may be in certain applications), where duplication may sometimes be a source of error. The term "metadata" as used herein generally refers to data about data. It may also be desirable in some embodiments to restrict or prohibit the ability to overwrite data in array file 407. Preferentially, new information may be appended to the file providing the benefit of traceability, and data integrity (i.e. as may be required by some regulatory agencies). For example, array file 407 may be associated with one or more implementations of an embodiment of probe array 140, where array file 407 acts to unify data across a set of probe arrays 140. Array file 407 may be created by applications 372 via a registration process, where user 101 inputs data into applications 372 via one or more of GUI's 246. In the present example, array file 407 may be associated with a custom identifier such as a machine readable identifier that could include identifiers described in greater detail below. Alternatively, applications 372 may create array file 407 and automatically associate array file 407 with a machine readable identifier that identifies an embodiment of probe array 140. Applications 372 may employ various data elements for the creation or update of array file 407 from one or more library files, such as library files 274 or other library files, where the information may be provided by a manufacturer of probe array 140 and define characteristics such as probe location and identity; dimension and positional location (i.e. with respect to some fiducial reference) of the active area of probe array 140; various experimental parameters; instrument control parameters; or other types of useful information. In addition, array file 407 may also contain one or more metadata elements that could include one or more of a unique identifier for array file 407, human readable form of a machine readable identifier, or other metadata elements. In addition, the applications 372 may store data (i.e. as metadata, or stored data) that includes sample identifiers, array names, user parameters, event logs that may for instance include a value identifying the number of times an array has been scanned, relationship histories such as for instance the relationship between each .cel file and the one or more .dat files that were employed to generate the .cel file, and other types of data useful in for processing and data management.

For example, user 101 and/or automated data input devices or programs (not shown) may provide data related to the design or conduct of experiments. User 101 may specify an Affymetrix catalogue or custom chip type (a catalog array such as the Mapping 6.0 Array) either by selecting from a predetermined list presented in one or more of GUI's 246 or by scanning a bar code, Radio Frequency Identification (RFID), magnetic strip, or other means of electronic identification related to a chip to read its type. Applications 372 may associate the chip type with various scanning parameters stored in data tables or library files, such as library files 274 of computer 150, including the area of the chip that is to be scanned, the location of chrome elements or other features on the chip used for auto-focusing, the wavelength or intensity/power of excitation light to be used in reading the chip, and so on. Also, applications 372 may encode array files 407 in a binary type format that may minimize the possibility of data corruption. However, applications 372 may be further enabled to export array file 407 in a number of different formats.

Also, in the same or alternative embodiments, applications 372 may generate or access what may be referred to as a "plate" file. The plate file may encode one or more data elements such as pointers to one or more array files 407, and preferably may include pointers to a plurality of array files 407.

In some embodiments, raw image data is acquired from scanner 100 and operated upon by applications 372 to generate intermediate results. For example, raw intensity data 405 acquired from scanner 100 may be directed to .dat file generator 410 and written to data files (*.dat) such as .dat file 415 that comprises an intensity value for each pixel of data acquired from a scan of an embodiment of probe array 140. In the same or alternative embodiments it may be advantageous to scan sub areas (that may be referred to as sub arrays) of probe array 140 where raw intensity data 405 for each sub area scanned may be written to an individual embodiment of .dat file 415. Continuing with the present example, applications 372 may also include unique identifier assignor 460 that encodes a unique identifier for .dat file 415 as well as a pointer to an associated embodiment of array file 407 as metadata into each .dat file 415 generated. The term "pointer" as used herein generally refers to a programming language datatype, variable, or data object that references another data object, datatype, variable, etc. using a memory address or identifier of the referenced element in a memory storage device such as in system memory 370. In some embodiments the pointers comprise the unique identifiers of the files that are the subject of the pointing, such as for instance the pointer in .dat file 415 described above comprises the unique identifier of array file 407. Additional examples of the generation and image processing of sub arrays is described in U.S. patent application Ser. No. 11/289,975, which is hereby incorporated by reference herein in its entirety for all purpose.

Also, applications 372 may also include .cel file generator 420 that may produce one or more .cel files 425 (*.cel) by processing each .dat file 415. Alternatively, some embodiments of .cel file generator 420 may produce a single .cel file 425 from processing multiple .dat files 415 such as with the example of processing multiple sub-arrays described above. Similar to .dat file 415 described above each embodiment of .cel file 425 may also include one or more metadata elements. For example, assignor 460 may encode a unique identifier for each .cel file 425 as well as a pointer to an associated array file 407 and/or the one or more .dat files 415 used to produce the .cel file 425.

Each .cel file 425 contains, for each probe feature scanned by scanner 100, a single value representative of the intensities of pixels measured by scanner 100 for that probe. For example, this value may include a measure of the abundance of tagged mRNA's present in the target that hybridized to the corresponding probe. Many such mRNA's may be present in each probe, as a probe on a GENECHIP® probe array may include, for example, millions of oligonucleotides designed to detect the mRNA's. Alternatively, the value may include a measure related to the sequence composition of DNA or other nucleic acid detected by the probes of a GENECHIP® probe array. As described above, applications 372 receives image data derived from probe array 140 using scanner 100 and generates .dat file 415 that is then processed to produce .cel intensity file 425, where applications 372 may utilize information from array file 407 in the image processing function. For instance, .cel file generator 420 may perform what is referred to as grid placement on the image data in .dat file 415 using data elements such as dimension information to determine and define the positional location of probe features in the image. Typically, .cel file generator 420 associates what may be referred to as a grid with the image data in a .dat file for the purpose of determining the positional relationship of probe features in the image with the known positions and identities of the probe features. The accurate registration of the grid with the image is important for the accuracy of the information in the resulting .cel file 425. Also, some embodiments of .cel file generator 420 may provide user 101 with a graphical representation of a grid aligned to image data from a selected .dat file in an implementation of GUI 246, and further enable user 101 to manually refine the position of the grid placement using methods commonly employed such as placing a cursor over the grid, selecting such as by holding down a button on a mouse, and dragging the grid to a preferred positional relationship with the image. Examples of grid registration and methods of positional refinement are described in U.S. Pat. Nos. 6,090,555; 6,611,767; 6,829,376, and U.S. patent application Ser. Nos. 10/391,882, and 10/197,369, each of which is hereby incorporated by reference herein in its entirety for all purposes.

As noted, another file that may be generated by applications 372 is .chp file 435 using .chp file generator 430. For example, each .chp file 435 is derived from analysis of .cel file 425 combined in some cases with information derived from array file 407, other lab data and/or library files 274 that specify details regarding the sequences and locations of probes and controls. The resulting data stored in .chp file 435 includes degrees of hybridization, absolute and/or differential (over two or more experiments) expression, genotype comparisons, detection of polymorphisms and mutations, and other analytical results.

In some alternative embodiments, user 101 may prefer to employ different applications to further process or perform higher level/specialized analysis such as analysis application 380. Various embodiments of analysis application 380 may exist such as applications developed by the manufacturer for specialized embodiments of probe array 140, commercial third party software applications, open source applications, or other applications known in the art for specific analysis or high level analysis of data from probe arrays 140. Applications 372 may be enabled to export .cel files 425, .dat files 415, or other files to analysis application 380 or allow enable access to such files on computer 150 by analysis application 380. Such functionality may be enabled by one or modules as described above with respect to plug-in module 373.

Additional examples of .cel and .chp files are described with respect to the Affymetrix GENECHIP® Operating Software or Affymetrix Microarray Suite (as described, for example, in U.S. Pat. No. 7,031,846 or U.S. patent application Ser. No. 10/764,663, both of which are hereby incorporated herein by reference in their entireties for all purposes). For convenience, the term "file" often is used herein to refer to data generated or used by applications 372 and executable counterparts of other applications such as analysis application 380, where the data is written according a format such as the described .dat, .cel, and .chp formats. Further, the data files may also be used as input for applications 372 or other software capable of reading the format of the file.

Some embodiments of applications 372 may be enabled to store and manage data stored in a file format or file based system. For example, a file based system may provide a high degree of flexibility over Database type storage formats where the database formats may require knowledge of a particular data model or organization of data in order to work effectively. In the present example, file based systems are not bound by such formatting constraints, thereby allowing greater flexibility to user 101 and developers of third party software elements. For instance, embodiments of application 380 enabled to process files generated by applications 372. In the same or alternative examples, user 101 and/or the third party developers may employ what are referred to as software development kits that enable programmatic access into file formats, or the structure of applications 372. Therefore, other software applications may integrate with and seamlessly add functionally to or utilize data from applications 372 that provides user 101 with a wide range of application and processing capability. Additional examples of software development kits associated with software or data related to probe arrays are described in U.S. Pat. No. 6,954,699, and U.S. application Ser. Nos. 10/764,663 and 11/215,900, each of which is hereby incorporated by reference herein in its entirety for all purposes.

Some embodiments of applications 372 may employ a system of file management that employs a method or data structure that utilizes a unique identifier associated with each file and a system of pointers within files that identify relationships between the files. The presently described system has advantages over database type methods of storing and managing probe array information for a number of reasons. First, a file based system opens the results and data produced by the software platform to use by third party software. Second, the file based system allows users flexibility to organize and store data in a manner that is preferred by the users and more amenable to their work flow and data management. Third, in the presently described file based system, all data related to the experiments, probe arrays, results, etc. is stored in the files. In other words, there are no separate databases of experiment information or the like that must be queried to obtain needed data for processing.

Embodiments of the unique identifier are independent of file names or other commonly used identifiers. One advantage of associating a unique identifier with each file is that it allows for the changing of file names by user 101, where the unique identifier still allows the file to be organized in a particular relationship with other files independent of the file name. For example, some management systems employ the name of a particular file to track and identify the file such that the relationship with a first file to one or more other files is dependent upon the name of the first file. In the present example, name of the first file is changed or modified in any way, the relationships to other the one or more other files may be lost. Whereas utilizing a unique identifier embedded as metadata within the file may be protected from overwriting and thus the integrity of relationships that depend upon the identifier is more stable.

Methods of generating unique identifiers may be accomplished in a variety of ways and can include a variety of non-random elements such as one or more of time based identifiers, machine or system identifiers, network identifiers, laboratory identifiers, user identifiers, identifiers particular to the experiment or application, or site based identifiers. Other elements of a unique identifier may also include one or more randomly generated identifiers, or other types of random and non-random identifiers known to those of ordinary skill in the related art. Those of ordinary skill in the art will appreciate that a unique identifier may comprise one or more of the elements described above or any combination thereof. For example, applications 372 may employ algorithm that generates unique identifiers comprising a plurality of elements arranged in a particular order. The elements may include elements in the following arrangement: Time-Network Address-Random-Random. In the present example, the arrangement of elements may comprise a string of characters and the time element may include a reference to system time (i.e. computer system such as computer 150), Greenwich Mean Time, or other standard time reference and the random elements may comprise strings of random characters such as numbers, letters, symbols, or other commonly employed characters.

In the presently described embodiments, the relationship between files may be arranged in a variety of ways. In one embodiment, applications 372 employs a file management data structure organized in a hierarchical-like format such as for instance a tree-like hierarchical structure where a primary file(s) comprises the "root" of the tree structure and subsequent tiers of files represent dependencies of each file on the data in the file from the tier or tiers above. Typically, the tiers may be viewed as having a "parent-child" type relationship where each parent file in a respective tier may have one or more child files in the tier below such as for instance each .dat file may be the parent to one or more .cel files in the tier below. Advantageously, the described file management structure provides user 101 with complete downstream traceability of files derived from information in the root file and tiers above. The present example of a hierarchical structure is used for the purposes of explanation of the nature of relationships between files and should not be confused with other types of tree-like data structure known in the art. For example, the .dat file may be considered the root file for all subsequent downstream files where a second tier comprises one or more .cel files derived from the .dat file, and a third tier may comprise one or more .chp files derived from each .cel file, where a file in each respective tier comprises a pointer to the child file in the tier below, and all files comprise a reference to the unique identifier associated with a common array file. In the present example, one or more .cel files may be processed from a single .dat file where each .dat file includes a pointer to the unique identifier of the .cel file. Further, one or more .chp files may be generated from each .cel file where each .chp includes a pointer to the unique identifier of the .cel file from which it was generated, and in some embodiments may also include a pointer to the .dat and/or array file from which the .cel file was generated.

Additionally, embodiments of applications 372 may include file indexer 450 that utilizes and maintains a small (i.e. maintains a minimal amount of information) database for the purpose of searching and identifying files or specific data elements of interest. Such a database may include cache database 455 that comprises data that duplicates data computed earlier and/or stored elsewhere. For example, it may be advantageous to provide cache database 455 for use in searching for files or specific elements contained within the files such as the .dat, .cel, .chp, and array files. In the present example, cache database 455 comprises the metadata of each file organized in the database according to a preferred data model. Additional data stored in cache database 455 for each file could also include memory addresses, current file names, file size, date/time stamps, electronic signatures, or other information that does not include probe array data such as raw or processed intensity values. Such a database provides an advantage because the alternative is to open each of the files until the desired information is obtained. In some embodiments, indexer 450 comprises a search engine to find various files or specific data elements within the database. Also user 101 may employ an implementation of GUI 246 to create search queries for files or specific data elements where input/output manager 430 may provide GUI 246 and direct search queries to indexer 450.

Analysis Application 380: Analysis Application 380 may comprise any of a variety of known or probe array analysis applications, and particularly analysis applications specialized for use with embodiments of probe array 140 designed for genotyping applications. Additional examples of genotyping analysis applications may be found in U.S. patent application Ser. Nos. 10/657,481; 10/986,963; and 20050287575; each of which is hereby incorporated by reference herein in it's entirety for all purposes. Typically, embodiments of applications 380 may be loaded into system memory 270 and/or memory storage device 281 through one of input devices 240.

Some embodiments of applications 380 include executable code being stored in system memory 270, illustrated in FIG. 3 as instrument control and analysis applications executables 380A. As illustrated in FIG. 4, Analysis Application Executables 380A may receive one or more files from input/output manager 430. For example, Analysis Application Executables 380A may be capable of specialized analysis of processed data, such as the data in .cel file 425. In the present example, user 101 may desire to process data associated with a plurality of implementations of probe array 140 and therefore Analysis Application Executables 380A would receive a .cel file 425 for processed from each probe array. In the present example, manager 430 forwards the appropriate files in response to queries or requests from Analysis Application Executables 380A.

Analysis Application Executables 380A may receive each of .cel files 425 and analyze the data using one or more algorithms to determine a genotype call for each SNP represented by a probe set (i.e. set of one or more probes that interrogate the same target), and one or more measure of quality or confidence associated with the genotype call.

Analysis Application Executables 380A may in preferred applications analyze all .cel files 425 in parallel, where for instance higher quality results may be obtained using the combination of data elements from each .cel file 425. Initially, Analysis Application Executables 380A will "normalize" the intensity data from each of files 425. The term "normalize" as used herein generally refers to performing a process of comparing and adjusting intensity values in each .cel file to a same scale or range such that the intensity values from each of the files is comparable to one another. Analysis Application Executables 380A may employ a variety of normalization methods that may include but are not limited to quantile normalization, or sketch normalization.

In some embodiments, Analysis Application Executables 380A may also determine an initial assignment for each SNP genotype using a variety of methods. In some embodiments, Analysis Application Executables 380A may perform this function in parallel to the normalization described above. For example, Analysis Application Executables 380A may employ what is referred to as Dynamic Modeling (DM) methods to make the initial assignment of genotype, where the intensity values are fit to models, and the genotype is determined by the best fit of the data for each SNP to a particular genotype model. Additional examples of dynamic modeling algorithms are described in U.S. patent application Ser. Nos. 10/657,481; 10/986,963; and Ser. No. 11/157,768; incorporated by reference above.

Analysis Application Executables 380A then identifies a minimum number of instances of each of the three genotype calls (i.e. AA, AB, BB) for the initial assignments and uses these identified instances to estimate the prior distribution on typical cluster centers and variance-covariance matrices. Next, Analysis Application Executables 380A may process the data associated with each SNP by combining the cluster centers and variances with the data employing what is referred to as a Bayesian method (see "Bayesian Data Analysis," by Andrew Gelman, John B. Carlin, Hal S. Stem, and Donald B. Rubin, hereby incorporated by reference in its entirety for all purposes, 2nd edition, Boca Raton, Fla.: Chapman & Hall/CRC, c2004) to derive a posterior estimate of cluster centers and variances. Lastly, Analysis Application Executables 380A assigns a genotype and confidence score for each SNP according to what is referred to as its Mahalanobis distance (distance resealed by the variance & covariance) from the three cluster centers.

Analysis Application Executables 380A may return the genotype values to Instrument control and image processing applications 372 for processing into a file format or alternatively Analysis Application Executables 380A may generate a file. Some or all of the SNP results including the genotype calls and/or confidence values may also be presented to user 101 in one or more GUIs 246.

Highly accurate and reliable genotype calling is an essential component of any high throughput SNP genotyping technology. BRLMM, the commercial method for the Mapping 500K product sold by Affymetrix, Santa Clara, is effective, but requires the presence of mismatched probes (MM) probes on the nucleic acid array to create "seed" genotypes (seed genotypes are another term for initial assignments). One embodiment of the present invention is a method that only uses perfect-match probes, BRLMM-P. One difference between BRLMM-P and BRLMM is that BRLMM-P derives seed genotypes directly from the clustering properties of the data (as opposed to BRLMM's reliance on initial genotype seeds from a software called "Dynamic Model" or DM (See U.S. Ser. Nos. 10/657,481; 10/986,963; and 11/157,768 previously incorporated by reference). Other differences exist, such as using only the most informative dimension for clustering and some modifications to the exact choices for likelihood function.

As an extension of the RLMM concept, one presently preferred embodiment, BRLMM-P (like BRLMM) performs a multiple chip analysis, enabling the simultaneous estimation of probe effects and allele signals for each SNP. See the following references which are incorporated in their entireties for a disclosure of RLMM concept; Xiaojun Di, et al., "Dynamic model based algorithms for screening and genotyping over 100K SNPs on oligonucleotide microarrays". Bioinformatics 2005 21(9):1958-1963; Nusrat Rabbee and Terence P. Speed, "A genotype calling algorithm for Afjymetrix SNP arrays" UC Berkeley Statistics Online Tech Reports, August 2005 and Nusrat Rabbee and Terence P. Speed. "A genotype calling algorithm for Afjymetrix SNP arrays" Bioinformatics Advance Access published online on Nov. 2, 2005.

Figure 5:
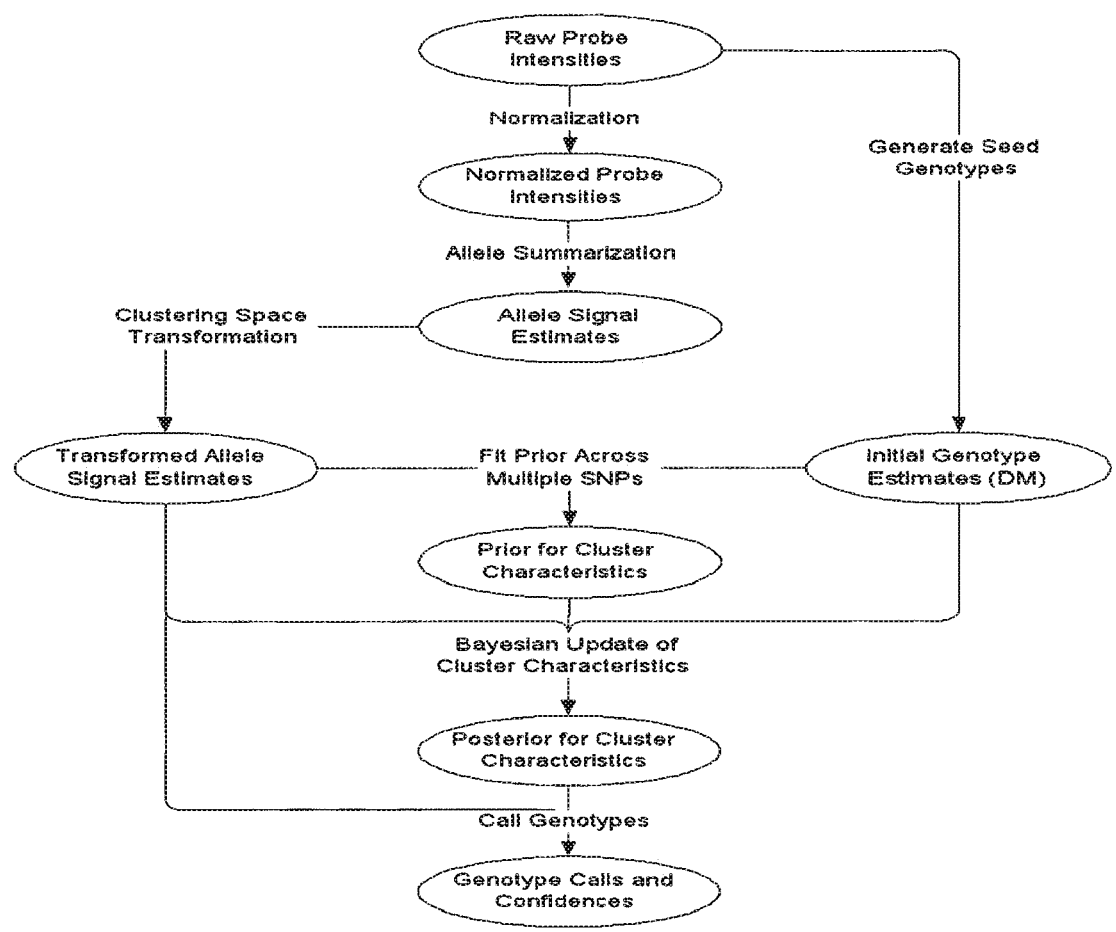
FIG. 5 is a workflow diagram for a preferred embodiment.
Figure 6:
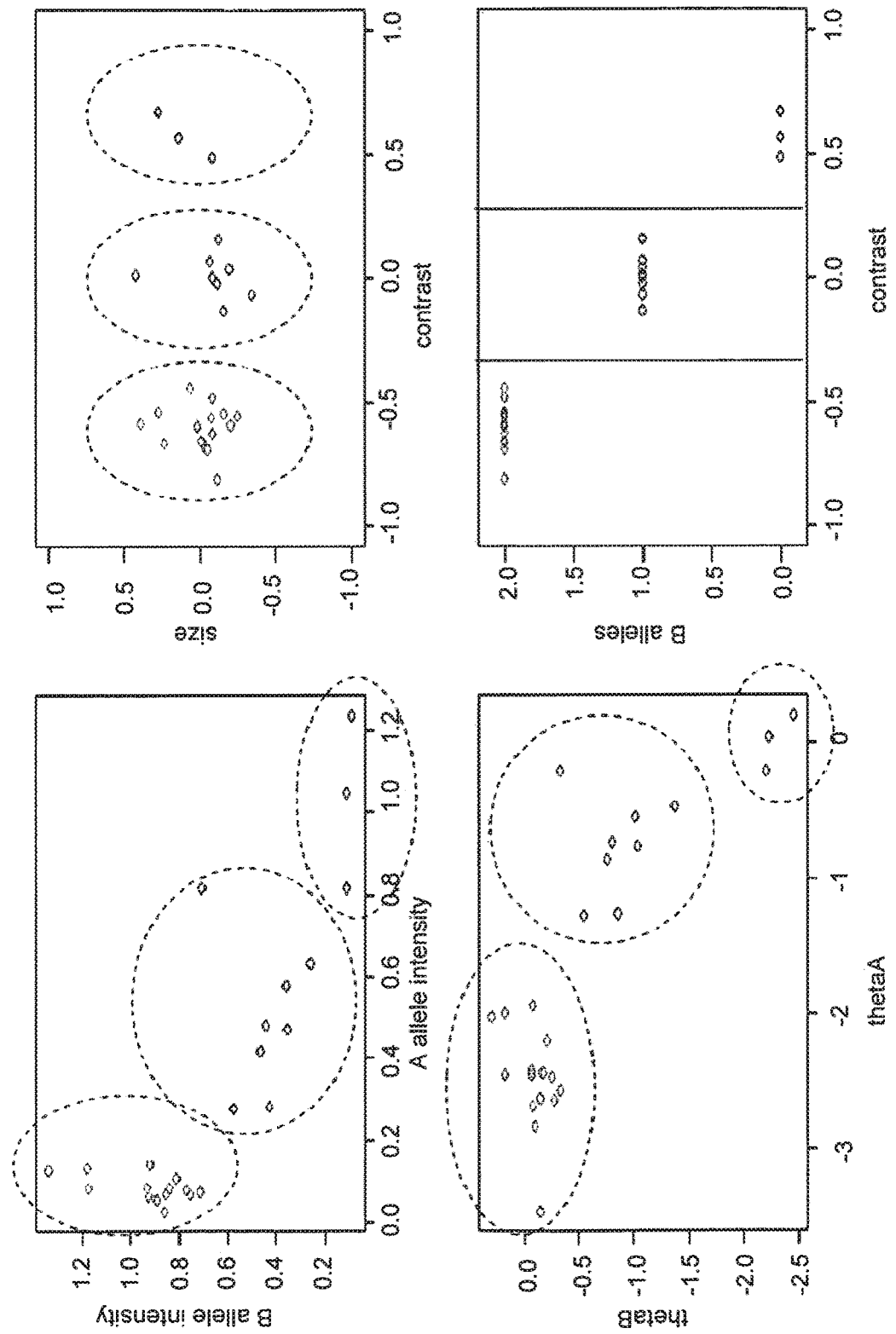
FIG. 6 shows a method of the present invention which calls genotypes by only using the "contrast" values for each data point.

FIG. 5 presents an overview of the BRLMM-P approach, which is one aspect of the preferred embodiment. The first step is to normalize the probe intensities and estimate allele signal estimates for each SNP in each experiment. The allele signal estimates are then transformed to a 2-dimensional space in which the underlying genotype clusters are 'well behaved' in terms of having similar variance for each of the clusters. Since the primary discriminator of genotype is the "contrast" dimension, the "size" dimension is discarded. In the resulting I-dimensional space, for each SNP, we evaluate the posterior likelihood of all plausible divisions of the observed data into three (or fewer) seed genotypes using a Gaussian likelihood model combined with prior information. The highest likelihood divisions of the data into plausible genotypes are retained, and combined to form a final estimate of seed genotype assignments. These final seeds are combined with the data to form a posterior distribution summarizing the best current estimate of genotype cluster center and variance for the SNP. Finally, a genotype and confidence score are assigned for each observation according to the relative distance to the cluster centers.

We now briefly discuss the general means for efficiently implementing the computations used by BRLMM-P before going into specific details. In one currently preferred embodiment, we have the goal of assigning genotypes BB, AB, AA to N data points obtained from chips hybridized to samples. In this embodiment, this can be accomplished efficiently and accurately using a technique designed to optimize clustering metrics. One preferred embodiment is called BRLMM-P and the algorithm workflow is shown in FIG. 5. The methods embodied in BRLMM-P can be divided into two types: first, the choice of the clustering metrics used to evaluate a potential assignment, and second, the efficient evaluation of such assignments to find a sufficiently good assignment of genotypes.

A typical set of clustering metrics is to use the log-likelihood of the data under a Gaussian cluster model. In one embodiment, there are three clusters corresponding to the three genotypes, each cluster is assumed to be approximately normally distributed with an individual mean and variance, and the log-likelihood of a given data point assigned to a cluster is the usual Gaussian log-likelihood. For such clustering metrics, in one embodiment of the method, the task is to find an assignment of datapoints to genotypes so that the log-likelihood is maximized. However, the naïve approach is computationally infeasible, requiring evaluation of an exponential number of possibilities. The BRLMM-P method therefore exploits the structure of the problem to efficiently optimize over plausible genotypes.

For example, given N data points, there are $3^N$ possible genotypes that can be assigned to those points (BB, AB, or AA). However, there is often a natural ordering of the data (i.e. more B allele to less B allele intensity) which leads to only $O(N^2)$ plausible labels for the data points (i.e. $BB^a\ AB^b\ AA^c$), because the AA genotype is always to the "right" of the AB genotype, which is always to the "right" of the "BB" genotype (when plotted as a difference between A alleles and B alleles). This implies it is possible to efficiently examine all $O(N^2)$ plausible assignments, and evaluate which genotype assignment fits the data best, in order to genotype samples.

In particular, with the use of running sums, we can evaluate mean and variance of genotype clusters, and compute log-likelihoods, in $O(1)$ time per plausible labeling, for $O(N^2)$ overall time. That is, given N+1 numbers (O, z1, ..., zn), the method can compute their running sums (O, z1, z1+z2, z1+z2+z3, ...) in $O(N)$ time, and compute the mean of a set of data zi ... zj in $0(1)$ time by simply subtracting the ith running sum from the j+1st running sum, rather than adding zi, ... zj. Similarly, the method can compute the variance using running sums of squares. Thus, the method can evaluate any labeling in $0(1)$ time per labeling, provided that the method is computing likelihoods depending only on the mean, variance, or other quantities that can be computed by running sums. This therefore allows the overall time cost of the method to be $0(N^2)$.

Unlike EM (iterative expectation-maximization methods), which moves from cluster assignment to cluster assignment iteratively improving the fit (a universal method), this procedure evaluates >all< plausible assignments of three genotypes to the data (specifically tuned for this problem). This prevents the method from being stuck in a local minimum, or failing to make progress due to a bad initial assignment of trial genotypes.

The remainder of the discussion below, steps through each of the above steps in detail and then presents a detailed assessment of BRLMM-P performance.

FIGS. 6-12 show a method of the present invention which calls genotypes by only using the "contrast" values for each data point. This is a one-dimensional clustering problem in contrast space. There is no need for a Dynamic Model algorithm to provide seed genotypes for this clustering method, because it tries all plausible assignments of seed genotypes, and picks the one that makes the observed data most likely. The present method fits the data using Gaussian clusters (one per genotype) and fits the (transformed) data in 1-D contrast space. See FIG. 6. The log-likelihood of the data given the clustering is used to decide which trial genotype is best.

Figure 7:
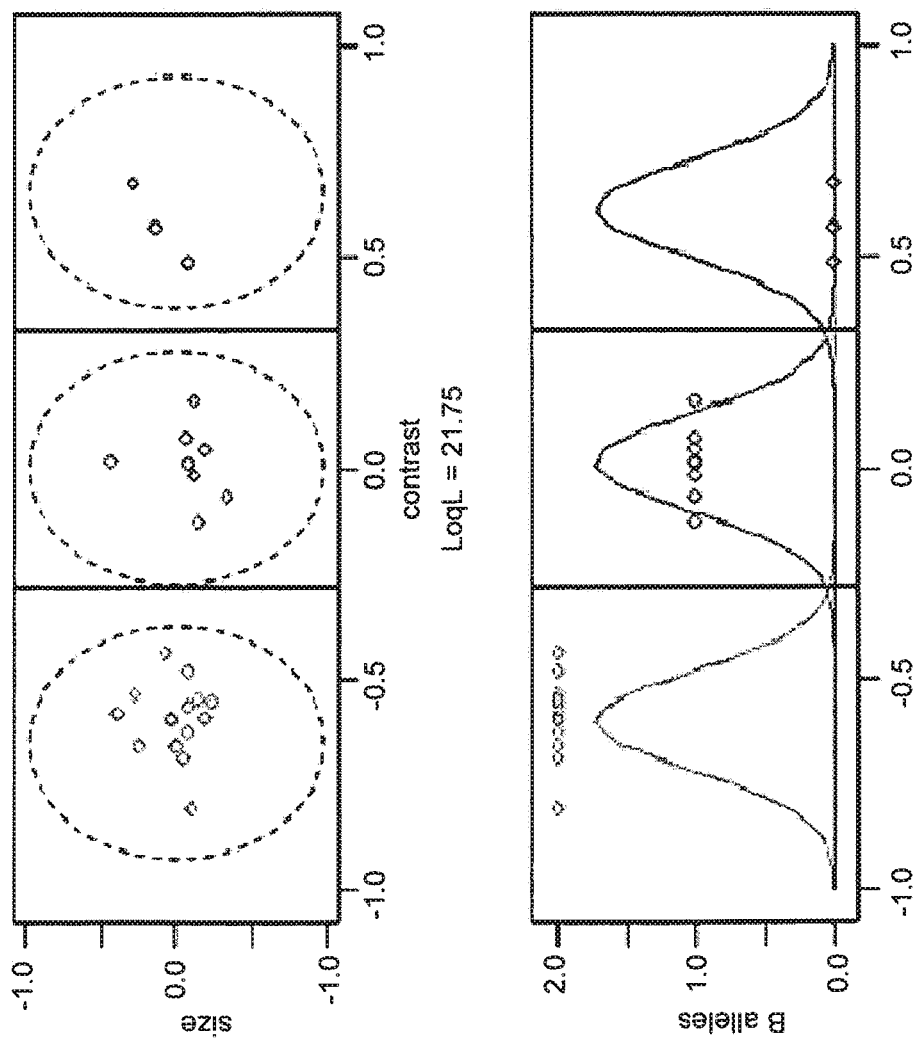
FIG. 7 shows a method for dividing data into trial genotypes.

The data is divided into trial genotype assignments as shown in FIG. 7. The trial genotype assignments are read from left to right as BB(2)→AB(1)→AA(0) (Green=BB, Red=AB, and Black=AA). Each genotype cluster has a mean which is the weighted combination of data plus prior knowledge. If there is no observed data for a genotype, then the cluster parameters are inferred using only the prior data. If there is a large quantity of observed data for a genotype, then the effect of the prior on cluster parameters is minimal, and the parameters are mostly obtained from the observed data. In the typical embodiment, the variance parameter is fitted to all three clusters to be the same value. The log-likelihood shows how well the data fits the assignment resulting from this division.

Figure 8:
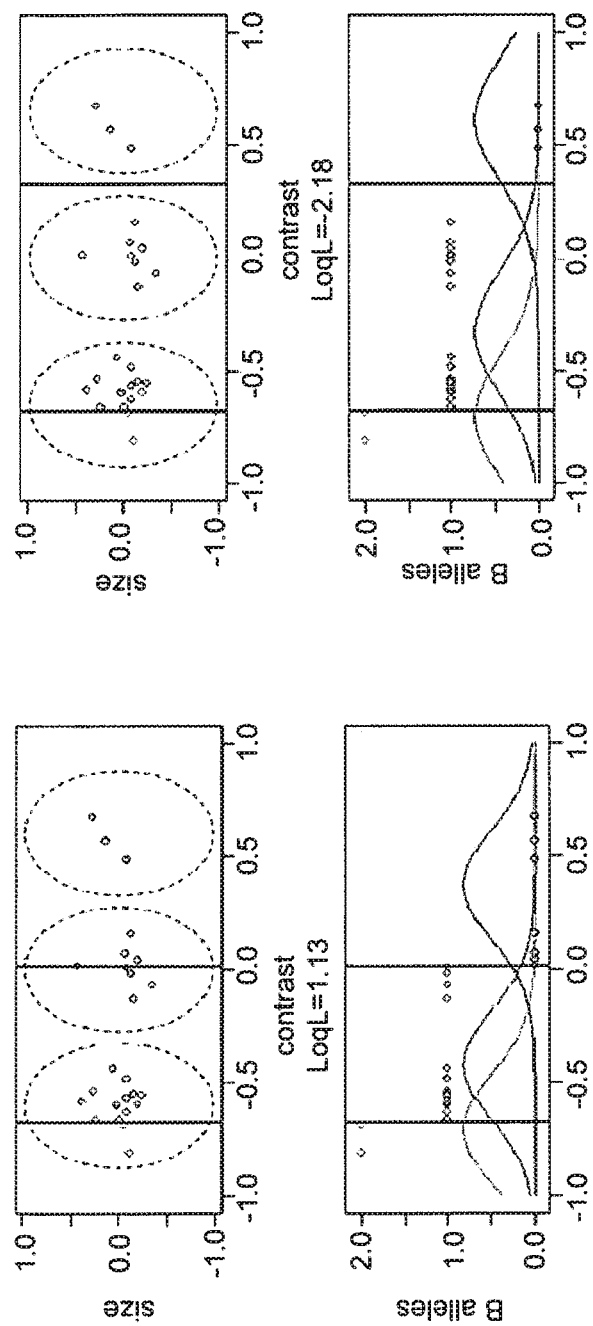
FIG. 8 shows dividing lines for trial genotype seeds.
Figure 9:
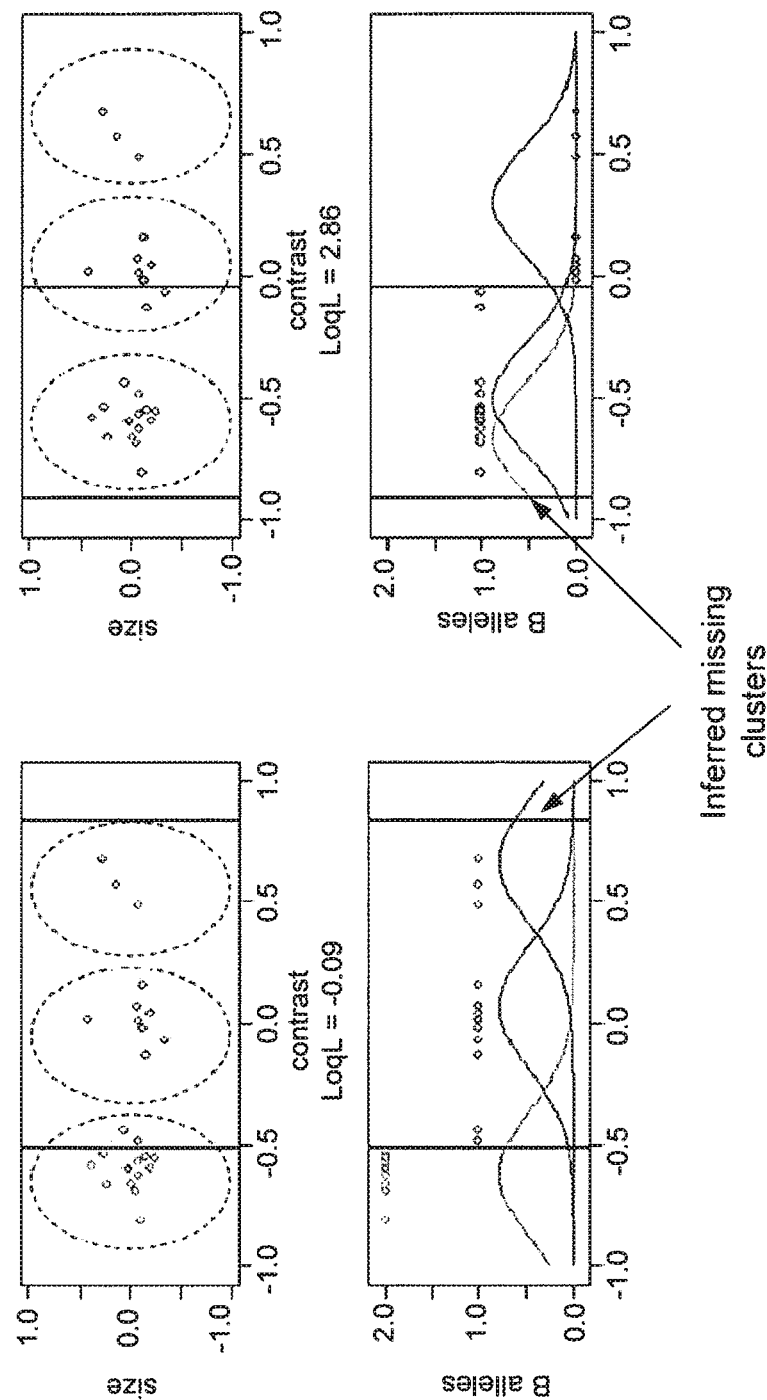
FIG. 9 shows the use of a prior to infer a missing cluster.
Figure 10:
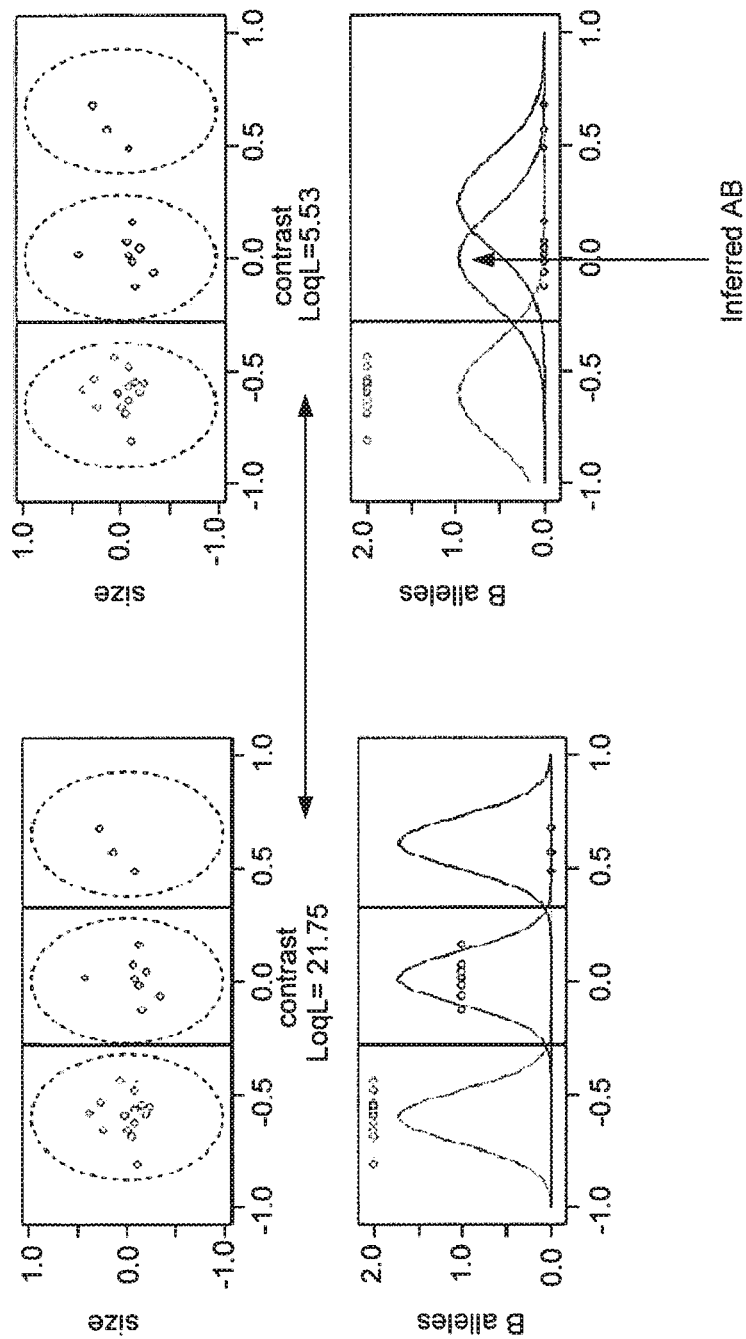
FIG. 10 shows that one method tries all $(n+1)(n+2)/2$ possible divisions of the data as trial genotype assignments, and the fit is evaluated by loglikelihood of data.

FIG. 8 shows two dividing lines for trial genotype seeds: BB(2)→AB(1)→AA(0). When there are fewer than 3 seed genotypes, the missing cluster must be inferred from the prior. See FIG. 9. The method tries all (n+1)(n+2)/2 possible divisions of the data as trial genotype assignments, and the fit is evaluated by loglikelihood of data as in FIG. 10. Once the log-likelihood is evaluated for each trial division of the data, the method infers final genotype cluster centers and variance from a weighted combination of the most likely divisions of data. Prior information is used to fill in the cluster parameters for genotypes not observed in the data.

Figure 11:
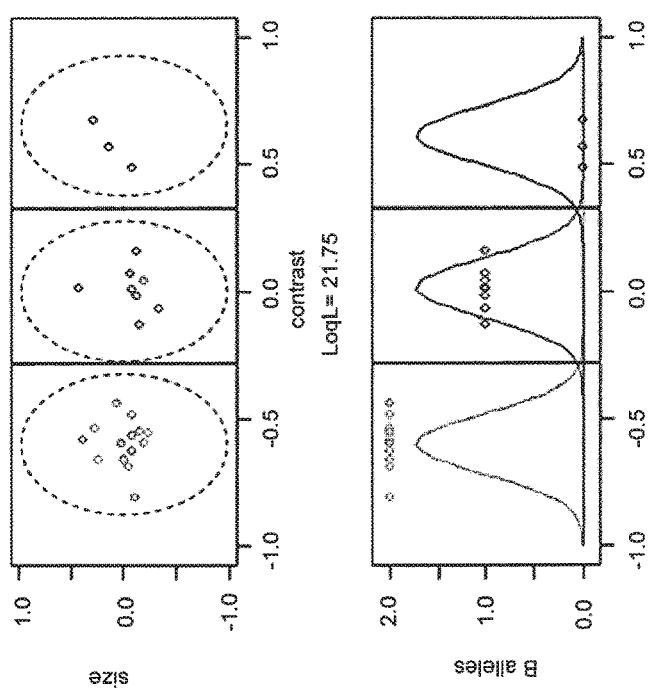
FIG. 11 shows genotype confidence calls.
Figure 12:
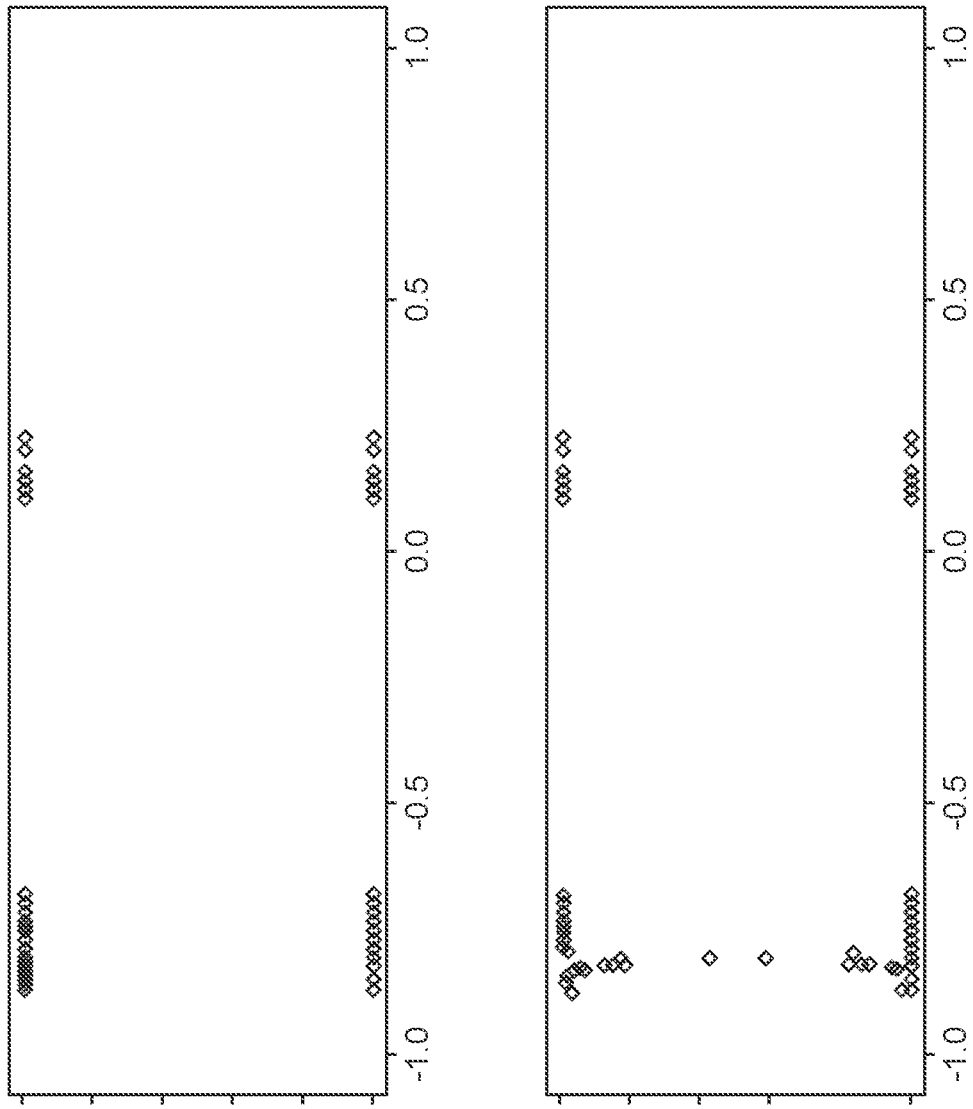
FIG. 12 shows splitting of two clusters into three.

Given the cluster centers and variances, the genotype for each data point is called and assigned a confidence based on the most likely cluster membership. This confidence score provides additional information beyond simply making a "call" of the genotype. Confidence scores indicating an uncertain genotype may be discarded by a downstream user to obtain only high-quality data. The confidence for the genotype calls is shown in FIG. 11. In one embodiment, the most probable cluster membership, X, (for three clusters X, Y, Z) is calculated by Pr(X)>Pr(Y)>Pr(Z), where Pr(X)+Pr(Y)+Pr(Z)=1. The confidence score is calculated by Pr(Y)+Pr(Z)=1−Pr(X). A confidence score near zero is a highly confident call for the genotype being X.

The above discussion has assumed that the clustering metrics are the basic Gaussian model. However, in practice, these metrics can be improved. One direction of improvement is to provide stronger assumptions on the structure of the clusters. A common problem with clustering methods is that increasing the numbers of clusters improves the likelihood. If there are only two genotypes present, on occasion the likelihood will be improved by finding three clusters. This may also occur due to the data not actually being distributed as the Gaussian model requires. See FIG. 12. This problem can be reduced using "hard-shell" restrictions of various types. In one implementation, cluster centers cannot be closer than some minimum value, in another, cluster centers that are too close lead to a penalty to the log-likelihood for that trial division of genotypes. Such constraints can provide "hard barriers" forbidding some labelings that would sub-divide clusters. Since such constraints (i.e. mean AA−mean AB must be larger than some minimum value) can be evaluated from the mean and variance alone, they do not contribute extra computation above $O(N^2)$ time.

There are also techniques designed to accommodate variations in how the data responds to the analysis and methods can be employed to customize the analysis in situations where the actual results do not fit what is observed. For example, the user can place a Bayesian prior on the likelihood, so that BB genotypes are likely to have high B allele probe intensities, and AB genotypes are likely to have intensities approximately balanced between B allele and A allele probes. Additionally, the labeling is performed with respect to some linear order—the likelihood evaluation can be done in a multidimensional space (i.e. one can use a log-likelihood for all 2*k probes in a probe set), without disturbing the $O(N^2)$ time. A SNP-specific prior can be placed on the likelihood, and use information previously obtained on the distribution of data. Again, since the Bayesian updates only use means and variances, they may be evaluated in $O(N^2)$ time using the above running sums techniques.

For additional efficiency, the $O(N^2)$ time can be reduced to O(N) time using binning techniques. For example, the method can "bin" points in [−1,1], into [−1,−0.99), [−0.99,−0.98], [0.99,1], and work with the summary statistics of each bin for evaluating the likelihood. This limits the computational load to $0(\# bins^2)$, which can be much smaller than N. (there is always an O(N) step to read in the data). Instead of outputting the "average labeling", one can do a single maximization step and compute the means and variances of each genotype and output those to use as a classifier for unknown data.

This preferred embodiment can provide a useful method of generating genotype assignments with high call rate and accuracy.

In the preferred embodiment, there are methods designed to customize the analysis for problems encountered in practice. For example, one potential problem with observed data is cluster shifting. The clusters for one data set may be positioned differently than the clusters from a prior set of experiments. This may be incorporated into the model by allowing some "wobble" in the cluster centers. This is easily incorporated by simply weakening the priors. Even if there are a large number of observations for a given genotype in the prior, do not increase the prior strength above some value (say, 10 observations equivalent strength).

Another method for customizing the analysis is to use isotonic regression instead of unconstrained Bayesian regression for the cluster centers. Isotonic regression is a general family of techniques designed to produce regression fits that maintain some monotonic property, such as always increasing or decreasing. The cluster centers should be in the order BB, AB, AA moving from left to right in contrast (difference) space. Ordinary Bayesian regression can lead to situations in which this constraint is not true, given odd data configurations. This may be solved by using a weighted form of isotonic regression on the cluster centers to find the "closest" valid configuration of cluster centers to the naïve cluster centers. In fact, we may further wish to constrain that AB>BB+delta and AA>AB+delta so that all cluster centers are separated by a minimum distance, delta. Let mB, mH, mA be the original cluster centers, with posterior weight wB, wH, wA (number of pseudo-observations). We may use the Pool-Adjacent-Violators algorithm to generate xB, xH, xA, new cluster centers satisfying our condition, and moving the clusters with the least support in the data the most. Let gamma=delta*(wB−wA)/(wB+wH+wA), and xB=mB−gamma+delta, xH=mH−gamma, xA=mA−gamma−delta. Now apply PAV, if (xB>xH){xB=xH=(wB*xB+wH*xH)/(wB+wH)}, if (xH>xA){xH=xA=(wH*xH+wA*xA)/(wH+wA), if (xB>xH){xB=xH=xA=(wB*xB+wH*xH+wA*xA)/(wB+wH+wA))). After this step, it must be the case that xB<xH<xA. Now update xB=xB+gamma−delta, xH=xH+gamma, xA=xA+gamma+delta. At this stage, now xB+delta<xH, and xH+delta<xA. Thus, the new cluster centers are separated by at least delta and are in the correct order.

An additional method to customize the analysis is to allow the variances to be different from one genotype cluster to another. The parameter "lambda" has been introduced to control the amount of mixing between cluster centers. The estimate of common variance between clusters=(wA*varA+wB*varB+wH*varH)/(wA+wB+wH), can be modified to varX=(wX*varY*(3−2*lambda)+wY*vary*lambda+wZ*varZ*lambda)/(wX*(3−2*lambda)+wY*lambda+wZ*lambda) for each cluster. Thus, the points in each cluster count more towards the estimate of that cluster, without necessarily requiring all clusters to have the same variance.

Another method for customization is to add BIC, the Bayesian Information Criterion to the cluster evaluation. This is a penalty to the likelihood for having observations in only one, two, or three genotype clusters. Each cluster observed penalizes the likelihood by k*log(n), where k is a tuning parameter (usually 2, for mean and variance) and n is the number of data points. This penalizes having more clusters than is justified by the data.

A further way to customize the analysis is to add a mixture frequency penalty to the log-likelihood. This is a penalty to the likelihood for having observations in clusters with low frequency. We add to the likelihood the "frequency" of observing data—each cluster has a number of observations r, and we add to the likelihood r*log(r). Over all three clusters, this is n*entropy of the distribution. We also penalize the decisions of calling a data point by adding the frequency to the likelihood of being in a cluster. This brings the likelihood closer to the standard mixture model. We can instead of using the observed frequency also use the prior number of observations as well for the likelihood (r*log(r+s)) where s is the prior strength.

Another consideration to add to the analysis is to address Standard Copy Number Variations (copy number variations that occur frequently enough amongst wild-type humans to require handling as special cases). ChrX is the classic example of this phenomenon where males have 1 copy (2 cluster centers) and females have 2 copies (3 cluster centers). Other examples are chrY, with 1 copy in males (2 cluster centers) and 0 copies in females (always no calls), and mitochondrial with 1 copy in all individuals (2 cluster centers). This can be handled by subsetting the samples based on estimated copy number of the SNP and fitting models only within copy number strata.

We discuss below some specific steps in the default embodiment of the invention, providing technical details beyond the above general discussion.

Normalization and Allele Summarization—FIG. 5 shows the BRLMM-P algorithm workflow. For example, the normalization and allele summarization steps of the BRLMM-P method consist of producing a summary value for each allele of a SNP in each experiment. The "A" allele summary value increases and decreases with the quantity of the "A" allele in the target genome, and similarly the "B" allele summary value increases and decreases with the quantity of the "B" allele in the target genome. These summary values are calculated to remove extraneous effects—chip-chip variation, background, and the relative brightness of different probes on the array. This section explains the technical details of this summarization process, which is similar to that used on expression arrays.

For each SNP of interest, the array contains multiple probes designed to hybridize to each allele of the SNP. The intensities of these features typically vary together in systematic ways for each genotype of the SNP. We therefore summarize these intensities in a single value for the features corresponding to each allele, the "signal" for that allele. (Note: due to crosshybridization with the alternate allele, this signal does not directly correspond to the concentration of the perfectly matched allele.) The intensities of the probes matched to the "A" allele are expected to decrease with decreasing quantities of the "A" allele, and similarly for the "B" allele probes. Since these change in opposite directions, we summarize the probes for each allele as independent signals. Therefore, for each SNP in each experiment, we obtain two values—an "A" signal and a "B" signal, which summarize the probes.

From the field of expression analysis on arrays, we know how to summarize several probes to a single signal value effectively. We need to account for extraneous effects on the probe intensity that vary from experiment to experiment (normalization), account for potential differences in background from chip to chip (background adjustment), and account for the systematic differences in feature intensity due to probe composition (feature effects). For the SNP 5.0 array (Affymetrix, Santa Clara, Calif.) the multiple features used to interrogate each allele have identical probe sequences, but even so we still use an approach that allows for systematic differences between probes from sources other than probe composition. While there are many options available for each of these effects, we have chosen to use standard solutions from the literature: quantile normalization at the feature level, no background adjustment, a log-scale transformation for the perfect match intensities, and a median polish (a robust method of fitting a model) to fit feature effects to the data obtaining a signal. This is exactly the same methodology that can be applied to summarize an expression array and produce a signal for a probe-set.

Quantile normalization is performed as in the literature, see Bolstad, et al., A Comparison of Normalization Methods for High Density Oligonucleotide Array Data Based on Bias and Variance, Bioinformatics 19, 2, pp 185-193. The intensities on each chip are ranked, and then the average intensity across experiments for each rank of intensity is substituted within each experiment for the given rank. [If R(I) is the rank of intensity within a chip, and Q(R) is the average intensity for a given rank, the quantile normalized intensity within a chip is Q(R(I))]. Because the quantile function is slowly varying and smooth, we approximate the Q(R) function for each chip with a linear interpolation for processing speed ["sketch" normalization]. This allows us to normalize millions of data points per chip rapidly with compact summaries of the data.

One preferred embodiment uses no adjustment for background. Unlike expression arrays, the target concentrations are well above background for the majority of the fragments containing SNPs. For this assay and genotype clustering algorithm background adjustment was not useful, and therefore the (normalized) perfect match intensities are used without adjustment for background.

To account for systematic differences in relative brightness between features, we fit the standard log-scale additive model to the probes for each allele separately: $\log(I_{i,j}) = f_i + t_j + \epsilon_{i,j}$, where fi is the effect due to feature i across experiments, tj is the effect with experiment j responding to the genotype of the SNP and the relative quantity of the fragment on which it is located (because of cross-hybridization to the other allele it cannot be interpreted as simply the effect due to the concentration of target for allele A), and $\epsilon_{i,j}$ is the multiplicative error for the observation. We fit this model using the standard median polish procedure for f and t, and for each experiment output the fitted value for t as the signal for that allele. For identifiability, we require sum(f)=0. The output signal value is retransformed to lie on the original linear intensity scale: signal=exp(t).

These stages constitute the normalization and allele summarization portion of the algorithm. At the end of these steps, we have for each SNP in each experiment two signal values: one for the "A" allele probe set, and one for the "B" allele probe set. Each SNP therefore has a 2×N matrix of values output –2 signals for each of N experiments. This output matrix is then used to evaluate each SNP for the genotype present in each experiment.

Clustering Space Transformation—Once we have signals for the two alleles of the SNP across all experiments, we evaluate distances between a prototype (cluster center) for a given genotype (AA, AB, BB) and the actual data seen in any one experiment. However, raw "signal" value, while very useful for expression analysis, is not perfectly suited for genotype cluster analysis (FIG. 6a). We transform each pair of signals for each experiment into a space with properties more suitable for evaluating genotypes.

Figure 13:
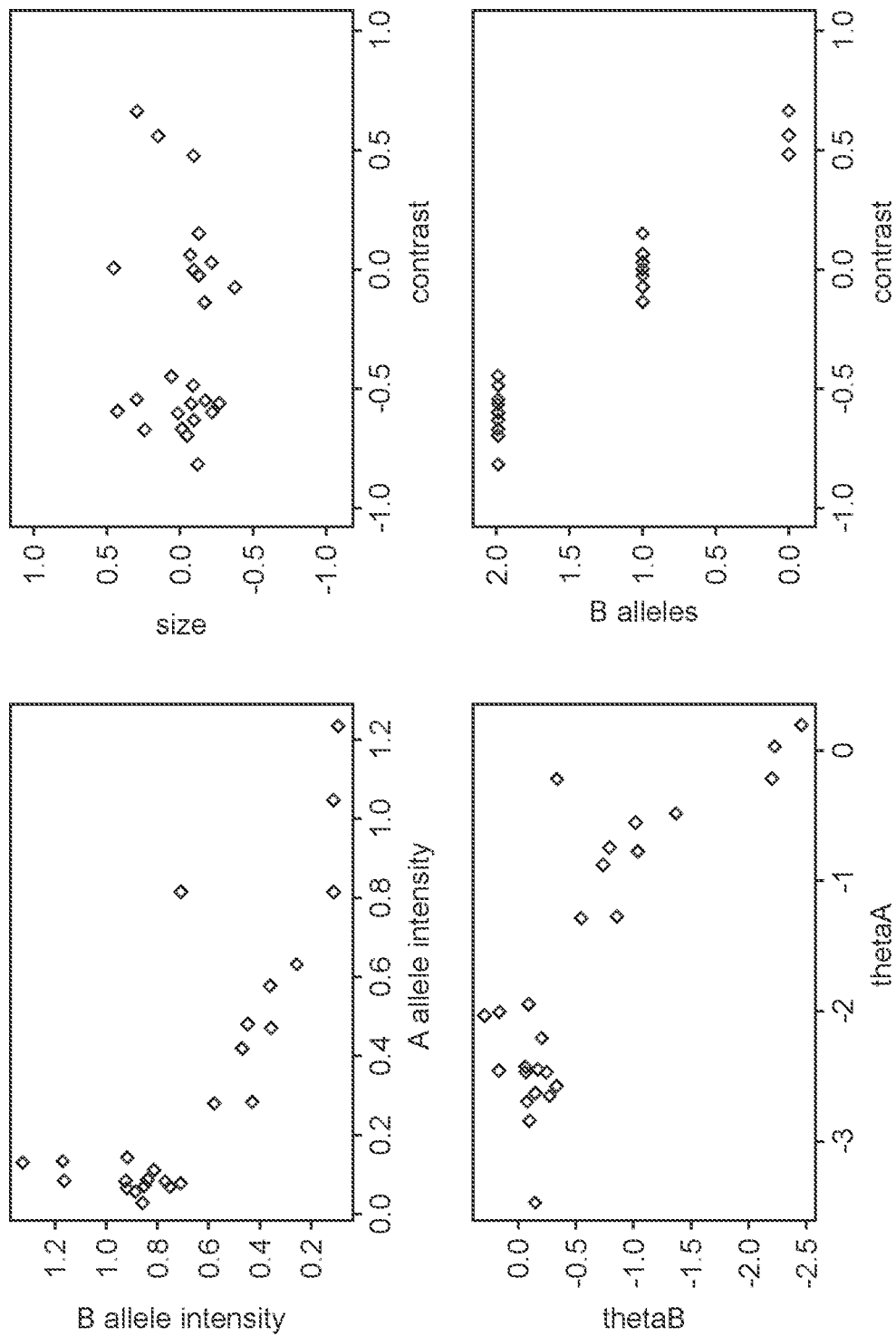
FIG. 13 shows clustering space transformation.

FIG. 13 shows Clustering Space Transformations. Here a simulated SNP (the data is artificial and used for illustration) is taken through the transformations used in BRLMM-P. The upper left shows summarized allele intensities, the lower left shows the log-transformed intensities, the upper right shows the transformation to contrast (sin h(K*(AB)/(A+B)/sin h(K)), and size (log(A+B)), and the lower right shows the assignment of the number of B alleles to each data point for a potential seeding. In all cases, BB points are green, AB are red, AA points are black with genotypes assigned by the design reference.

The desirable qualities for such a space include approximate independence of the difference between genotypes and the magnitude of signal, and controlling the variation within the various clusters to be comparable. For example, the standard "MvA" or "MA" transformation used to plot expression analysis could be applied to the two signals, resulting in M=log(SA)−log(SB) and A=(log(SA)+log(SB))/2. This isolates most of the difference between genotypes into the M axis, leaving a mostly irrelevant "brightness" component in the A axis. The MvA transformation is useful, but does not allow any fine tuning of cluster properties. One hazard is that the spread of homozygous clusters (where one allele is completely absent) can be very large if, after background adjustment, the resulting signal for that allele is near zero. Signals near zero can be extremely variable after taking logarithms, and the MvA transformation inherits this variability.

It is preferable to use a space in which the spread of homozygous clusters can be controlled, even when a signal estimate is near zero, and where the typical variation can be adjusted to be similar between heterozygous and homozygous genotype clusters. Let us define two axes: Contrast= (SA−SB)/(SA+SB) and Strength=log(SA+SB). Strength of course measures the overall brightness, which is mostly independent of genotype, and Contrast is a quantity that will depend most strongly on genotype ranging from −1 for the ideal BB genotype to +1 for the ideal AA genotype. However, while this transformation limits the range of the resulting value, and so limits the variation, there is no guarantee that the result of this transformation will have similar variation between the heterozygous cluster and the homozygous clusters. We further generalize the Contrast axis to define a Transformed Contrast=a sin h(K(SA−SB)/ (SA+SB))/a sin h(K), where K is a tuning constant. FIG. 7 shows the functional form of this transformation for different values of K. The effect of varying K is to change the amount of "stretch" of the difference between A and B signals when the difference is small (i.e. likely to be heterozygous), vs. the difference between A and B signals when the difference is large (i.e. likely to be homozygous), thus K can be used to balance the variability in homozygous and heterozygous genotypes and remove any heterozygous dropout. By experimentation across several data sets, it was ascertained that the value K=2 worked well to balance the variation of genotype clusters (FIG. 6d).

While many other transformations of the data could be used, this space worked well for clustering genotypes while avoiding heterozygous dropout. The "Contrast Center Stretch" (CCS) option was implemented within was the software, and cluster in this transformed signal space. The largest quantity of information about the genotype is contained within the contrast dimension, with minimal information about the genotype in the "size" dimension. For BRLMM-P, we only retain the contrast information for each SNP, and cluster in the resulting I-dimensional space.

Figure 14:
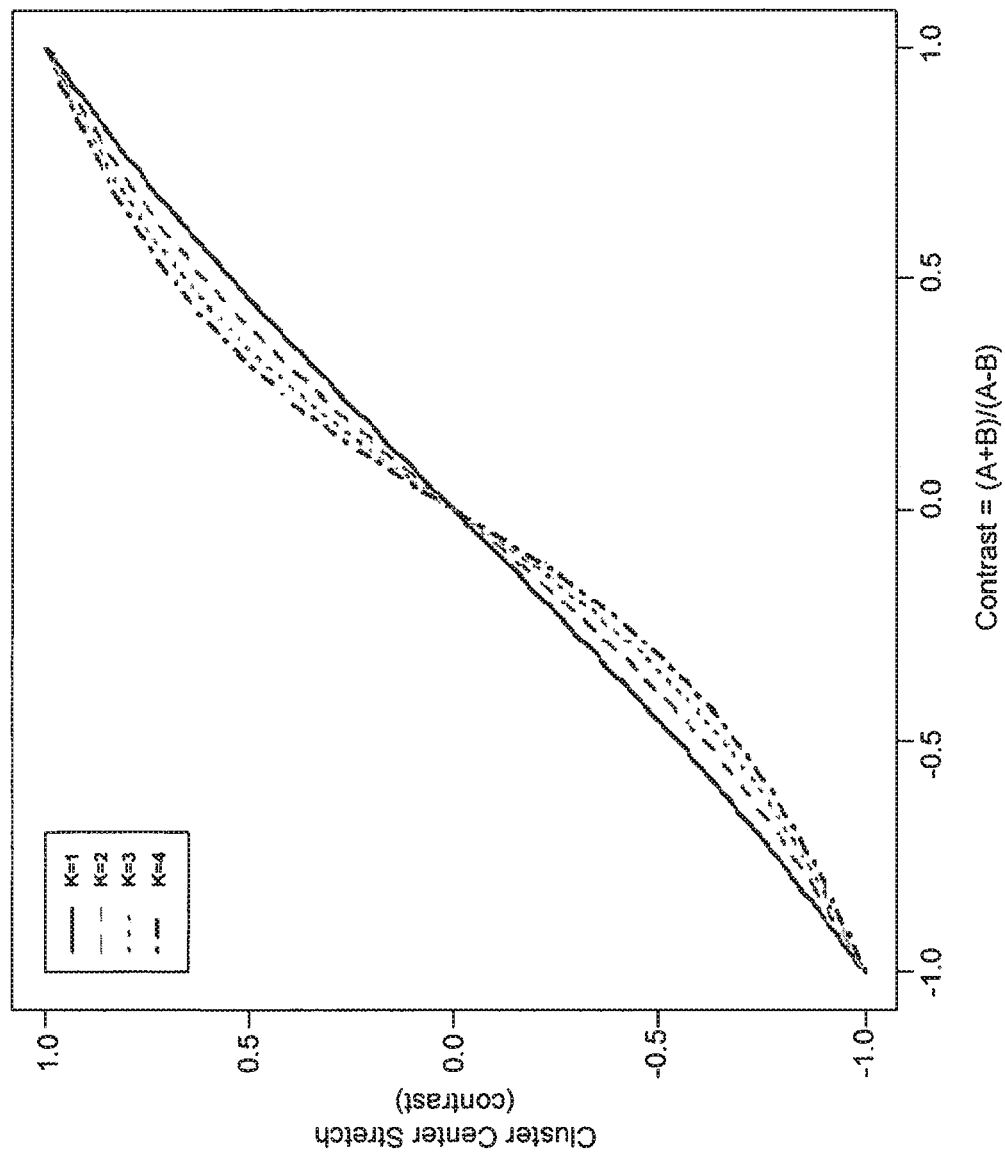
FIG. 14 shows an example of Cluster Center Stretch transformation.

FIG. 14: Examples of the Cluster Center Stretch (CCS) transformation. The CCS transformation is defined as a sin h(K*Contrast)/a sin h(K) where Contrast is defined as (SA−SB)/(SA+SB). The effect of the transformation is to stretch contrast values near zero (corresponding to heterozygous genotypes) and to compress contrast values near −1 and +1 (corresponding to homozygous genotypes). Higher values of K apply a more extreme transformation, setting K to 1 yields effectively an identity transformation. The value of K can thus be tuned to alter the balance between performance on homozygotes and heterozygotes, with higher K values making heterogenous calls more likely.

Calling Genotypes—genotypes are called by a template-matching procedure comparing the transformed allele signal values observed in an experiment to the typical values (prototype) we expect for each genotype. The genotype that is estimated to have the highest probability of having produced the data point is reported as the call. The approximate confidence for that call is the estimated probability that the data point belongs to one of the other clusters. This allows the genotype assignments to be ranked by quality, and hence make the decision not to call in cases of ambiguity.

Every autosomal SNP is expected to have three genotypes, "AA", "AB", and "BB" For each genotype for a given SNP, it is expected to have a prototype (typical observed values for that genotype, or cluster center), with some scatter of values around the prototype. In a preferred embodiment the scatter is approximated by a normal distribution (and the careful choice of the CCS transformation ensures this is a good approximation). For clusters of this type, the relative probability of belonging to a cluster is computed as a function of the distance from the cluster center and the variation within the cluster. The standard settings for BRLMM-P (which may be altered by advanced users) compute a common variance for all clusters.

Within any experiment, it is preferred to derive transformed contrast values x for a SNP and compare to the SNP-specific prior on cluster characteristics, the derivation of which is outlined in the following section. The SNP-specific prior includes three cluster centers μAA, μAB, and μBB with covariance matrices ΣAA, ΣAB and ΣBB, from which we obtain relative probabilities p(AA), p(AB), and p(BB). Note that we retain, where possible, similar notation to that used in the description of the prior BRLMM algorithm, though for BRLMM-P the covariance matrices are just scalar values since the clustering is performed in a one-dimensional space). We call the genotype of the SNP as the genotype with the highest probability, X, where P(X)>P(Y)>P(Z).

The confidence we assign to this call is P(Y)+P(Z), where P(X) is the estimated probability for the called cluster. This confidence is always between zero and 1 (in fact, it is difficult for it to be above 0.66). It is a rough measure of the quality of the call (but is not a "p-value"). We set a threshold for quality of 0.05 for a call/no-call decision, based on the performance on several test data sets. This can be adjusted by the user to tune the tradeoff between call rate and accuracy—see the results section for a comparison of performance at various thresholds.

Estimating Cluster Centers and Variances—The above section dealt with how to call genotypes and ascribe confidence values to those calls given an appropriate prototype. This section deals with how to derive these prototypes. This is achieved using a Bayesian procedure, in which we visit every SNP and combine a prior (estimate before seeing the particular data set, plus uncertainty in that value) for that SNP with the data observed to obtain a posterior estimate of cluster centers and variances. The prior may be a generic prior common to all SNPs, or a specific prior computed for that SNP from a set of training data. A prior has entries for the expected center of each genotype, the expected variance of each genotype, the uncertainty in those estimates (measured in 'pseudo-observations'), and covariances between those genotype centers. The posterior estimate has the same structure (mean, variance, uncertainty, and covariances). The posterior estimate is what is then used to call genotypes.

We do not know the actual division of the data into genotypes when combining the prior and the data. BRLMM solved this problem by using an external source of seed genotypes (DM) giving reliable data for a subset of data points. BRLMM-P solves this problem by evaluating all plausible assignments of 'seed' genotypes to the full set of data points with respect to their likelihood, and then averaging over the most likely seeds. That is, we repeatedly make a "hard" (every data point is assigned to exactly one genotype cluster) assignment of data points to "seed" genotypes, and evaluate the likelihood of the data under a Gaussian cluster model to evaluate the quality of this 'hard' assignment of genotypes to data points (this is similar to a K-means procedure). We combine the most likely 'hard' assignments into a "soft" (allowing a data point to be partially assigned to more than one genotype cluster) assignment of seed genotypes, which we treat as a reliable seed. Once we have a reliable assignment of seed genotypes, we can compute the posterior distribution of the locations of the three clusters.

We observe that plausible "hard" assignments of genotypes to data points have the following structure: sweeping from left to right in contrast space, we will always see some number (possibly zero) of BB genotypes, followed by some number (possibly zero) of AB genotypes, followed by some number (possibly zero) of AA genotypes. That is, the more copies of the B allele we have, the higher the relative intensity of the B probes relative to the A probes. Given the data, plausible genotypes are assigned as though there were two dividing contrast values (corresponding to vertical lines in contrast/size space) that determine the transitions between genotypes (BB to AB, and AB to AA).

Figure 15:
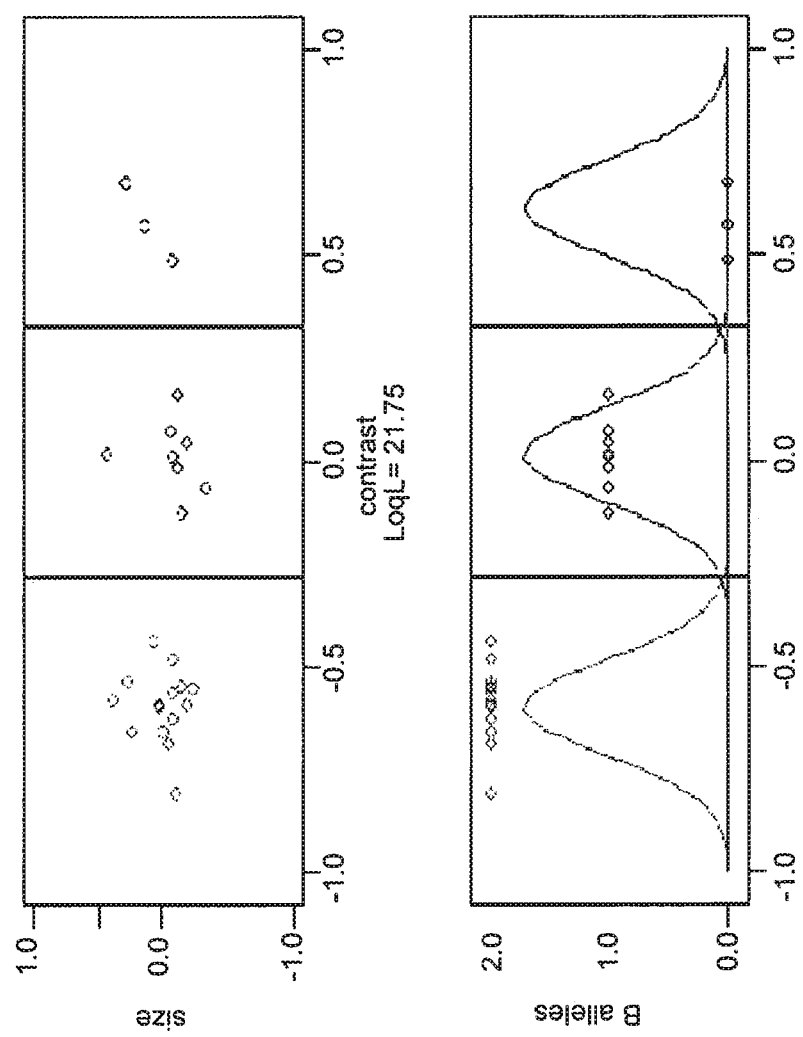
FIG. 15 shows an example division of simulated data.
Figure 16:
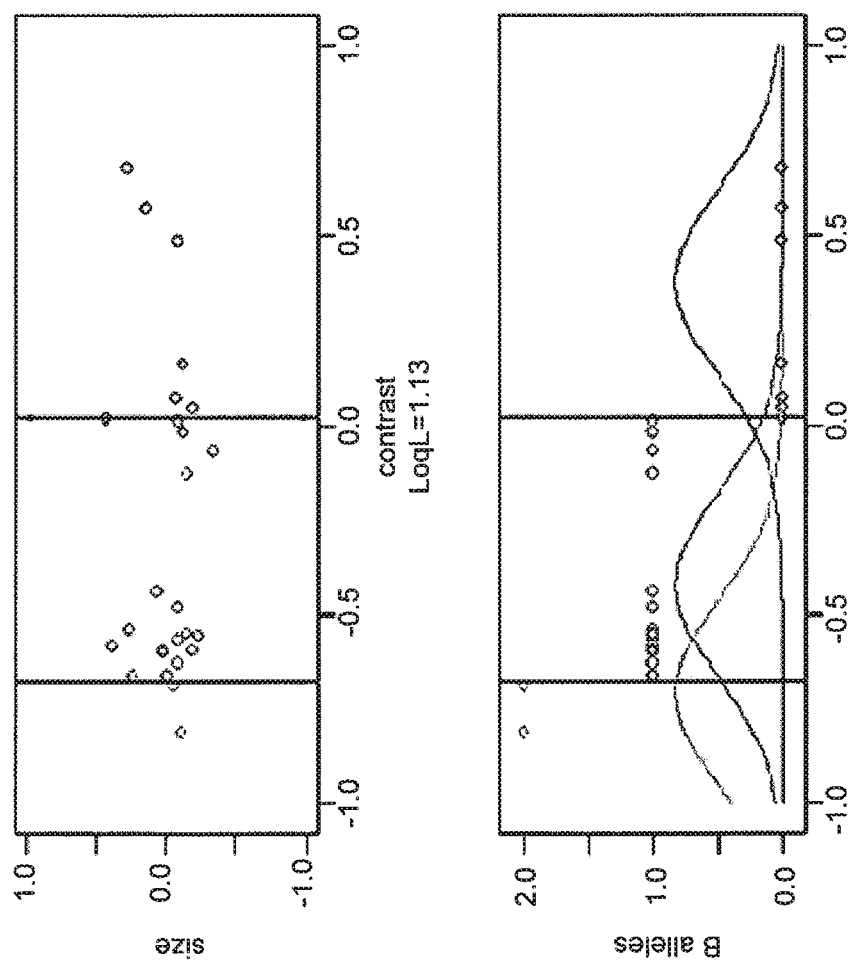
FIG. 16 shows another example of dividing the data.
Figure 17:
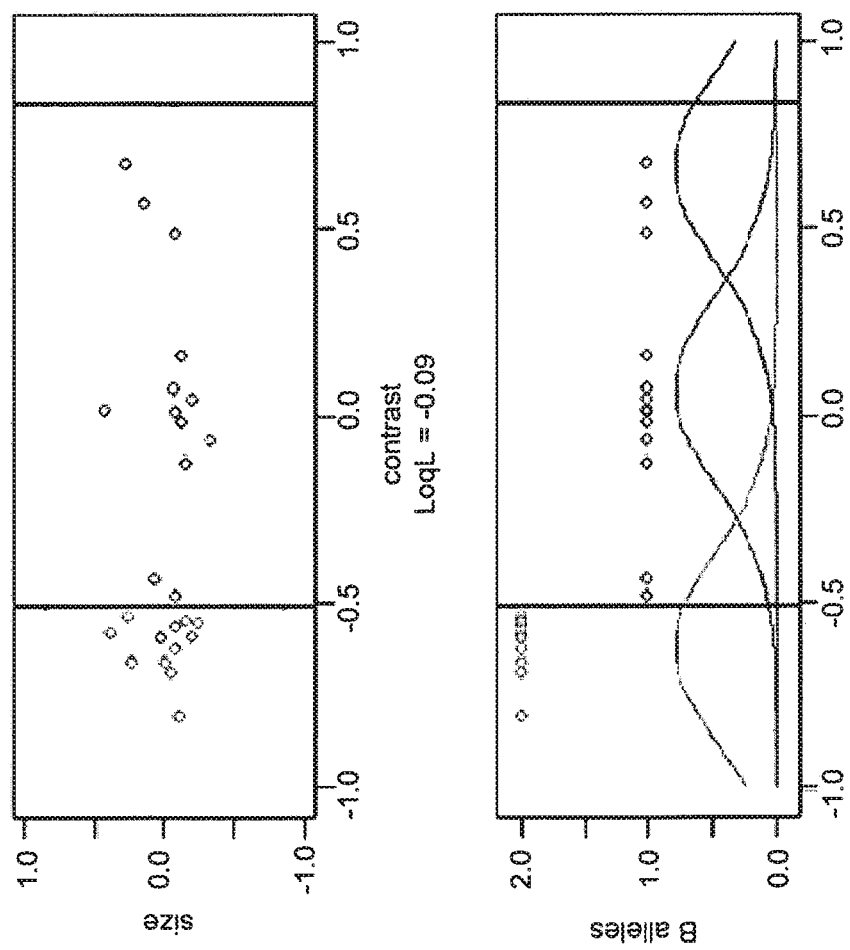
FIG. 17 shows a division of data that includes no AA genotypes.

FIG. 15 is an example division of (simulated) data. Two dividing lines divide the data into three assigned genotypes, BB in green, AB in red, and AA in black. Within each genotype, we compute a mean and variance, and combine with the prior to obtain a posterior estimate of mean and variance for each cluster. The log-likelihood of the data is computed given these distributions and the hard assignment of seed genotypes to clusters. FIG. 16 shows another example of dividing the data, with a lower likelihood. While a human eye can clearly see that dense clusters in the data are split, the computer must evaluate the likelihood of the data given this clustering to find that this is a suboptimal assignment of genotypes to data. FIG. 17 shows a division of the data that includes no AA genotypes (black, 0 B alleles). Note that there is still a computed mean and variance for the AA cluster, despite no seeds designated AA being present. This mean and variance is computed via the prior and is based on the prior center, as well as the covariances between cluster centers.

This implies that for N data points, there are only $(N+1)*(N+2)/2$ plausible ways of dividing the data into genotypes. Rather than following an iterative procedure (such as K-means or EM), we simply enumerate them all and thereby avoid any problems of being trapped in local maxima of the likelihood when looking at the fit to the data. This is not particularly time consuming because the use of Gaussian likelihoods allows us to evaluate each plausible assignment in $O(1)$ time by means of running sums. (We have employed additional computational methods that allow for linear scaling to large numbers of data points.) For BRLMM-P, we use the normal-inverse-gamma prior for the distribution of the mean and variance of each cluster center. (This differs from the semi-conjugate distribution used in BRLMM) If we denote: K=covariance matrix between cluster centers (expressed in pseudo-observations) S=variance of observations u=prior means; m=observed means; N=diagonal-number of observations in each cluster. Then for the conjugate prior, the variance of observations factors out of the updating formula for the cluster centers and results in the update formula: $(K^{-1}+N)^{-1}*(K^{-1}u+N*m)$. This is different from BRLMM in that we compute the shift in means without first constructing a SNP-specific variance matrix. The conjugate prior links the mean and variance of each cluster more tightly than the semi-conjugate prior used in BRLMM, and therefore simplifies the computation. This lightens the computational load of computing posteriors and is an advantage of using the conjugate prior rather than the semi-conjugate prior used in BRLMM.

Interpreting the formula, the cluster centers move to the average between the mean of the data, weighted by the number of observations of each genotype, and the prior location, weighted by the effective number of pseudo-observations provided in the prior. The variance is then computed as a weighted average between the observed variation, the prior variance, and the distance by which the centers have moved from the prior location. This Bayesian update has the sensible property that when there is little or no data available the estimate of cluster centers will be driven mainly by the prior estimate, u, and when there is a lot of data available for a given genotype the estimate will be driven by the observed means, m.

The complete computation loop looks like the following: for each plausible assignment of seed genotypes, evaluate the likelihood of the assignment given the posterior likelihood of the clusters. Given the likelihoods of all assignments, compute a relative probability for each data point to be each genotype (i.e. a "soft" assignment obtained by a weighted average over all plausible "hard" assignments). Use this resulting "soft" assignment to seed the final computation of the posterior distribution of centers and spread for each genotype. With these posterior estimates of center and spread for each cluster, genotypes and confidences are then determined as outlined in the previous section.

Special Cases—The preceding algorithm assumes that the observations for each SNP are well described by prototypes for each genotype. However, for SNPs on the X chromosome, there are distinct clusters for each gender due to males having one fewer copy of the X chromosome. This not only changes the location of the cluster centers for XY individuals, but the SNPs located on chrX may end up being called as heterozygote. We therefore treat the chrX SNPs differently for XX individuals than for XY individuals. Note that the special treatment of chrX SNPs described here is only applied to SNPs on chrX in the nono-pseudo-autosomal region, and for the rest of this section when we talk about chrX it is to be interpreted as chrX excluding the pseudo-autosomal region.

We detect the difference between XY and XX individuals by the distribution of observations in contrast space for all chrX snps. XY individuals are estimated as those where the distribution of all chrX SNP contrast values within the sample divides into three clusters by EM with fewer than 10% of chrX SNP values in the middle cluster. This decision rule allows for some frequency of misclassification of chrX SNPs when treating them uniformly, while robustly discriminating males from females in natural populations. The remaining individuals are classified as XX. For each chrX SNP, we treat XX individuals and XY individuals as separate data sets.

XX individuals are handled using the standard BRLMM-P methodology for all chrX SNPs, that is, three cluster centers are learned from the data along with within-cluster spread and used to classify observations. However, no data from XY individuals is used in this calculation. XY individuals are handled using a modification of the BRLMM-P methodology for all chrX SNPs. Only two cluster centers can be learned from the data (AA and BB), and only the data for the XY individuals are used. Therefore the following modifications are performed First, we only evaluate assignments of AA and BB genotypes as a "seed", and ignore the computed AB cluster completely for both likelihood and making genotype calls from the posterior. Thus, for XY individuals, only "AA" and "BB" genotypes are fit, and for any observed data, "AB" will never be called.

Fitting of XX and XY individuals separately improves the genotyping performance within each group. Modifying the prior for XY individuals to avoid heterozygous calls improves the genotyping performance for XY individuals. This is the justification for having a special purpose modification for chrX SNPs within BRLMM-P.

Another special case is that of a SNP with unusual behavior, such as a SNP with probes for the A allele having a different sequence than probes for the B allele (for example, the A allele probe could be from one strand and the B allele probe from the other strand). Such a SNP may have a very unusual location for the cluster centers when compared to the typical SNP on the array. This may lead to erroneous assignment of cluster identity if, for example, the AB cluster is located where the BB cluster is on a typical SNP. With sufficient data to show examples of all three clusters, such a mis-assignment will usually be corrected, however, for those SNPs with rare minor alleles, this may require a large number of samples.

To handle exceptional cases such as this and to improve the performance on more conventional SNPs, we allow for the provision of a SNP-specific prior for each SNP. This takes data (labeled and/or unlabeled) from a training set and provides information on where the training genotypes are located. This is very similar in effect to clustering the observed data with the training data, and requires that lab procedures be sufficiently similar between training and observed data so that they may be clustered together.

Pre-screening samples—In the typical workflow it is very useful to have a simple metric that can be computed based on a single experiment to determine if the experiment is of high enough quality to be considered as completed and ready for future multiple-sample analysis, or if it should be repeated. BRLMM-P yields very high quality genotype calls but it is inherently a multiple sample method, and the exact results for any given sample will depend in part on the batch in which the sample is analyzed, so it is not ideally suited for in-lab single-chip quality determination.

With this application in mind, we have taken advantage of the DM genotype calling algorithm [Xiaojun Di, al., "*Dynamic model based algorithms for screening and genotyping over* 100*K SNPs on oligonucleotide microarrays*". See U.S. patent application Ser. Nos. 10/657,481; 10/986, 963; and Ser. No. 11/157,768. Bioinformatics 2005 21(9): 1958-1963]. It is a single chip analysis method and call rates with DM are very strongly correlated with call rates and concordance when experiments are ultimately re-called with BRLMM-P or other multiple-sample genotype calling methods. The SNP 5.0 array has a set of 3,022 SNPs tiled with both PM and MM probes so that each chip can be analyzed with DM (at a confidence threshold of 0.33) to produce a call rate. We call this metric the QC call rate. The 3,022 SNPs tiled for calling with DM are a subset of the 500,568 SNPs on the Mapping500K product (1,511 from each of the Nsp and Sty arrays), see the netAffx Analysis center on the Affymetrix web site for more information, but they are not a random sample—the pool is intentionally enriched for SNPs that were more challenging to call in the Mapping500K to yield a more sensitive metric of quality.

The recommended protocol is that experiments with a QC call rate of 86% or better should be considered as complete and are expected to result in a call rate of 97% or better when recalled with BRLMM-P. Note that this threshold of 86% is specific to the SNP 5.0 array and the particular set of 3,022 SNPs tiled on it. QC call rates of 65%, 70%, 75%, 80% or 85% may also be acceptable.

The ideal way to assess performance would be to evaluate the tradeoff between accuracy and call rate in data generated from a collection of samples for which the true reference genotypes are available for all SNPs on the SNP5.0 or other arrays. Fortunately something closely approximating this has been made possible by the International HapMap Consortium—the phase 2 release provides reference calls on a collection of 270 samples for approximately 70% of the SNPs on array. If submissions to HapMap by Affymetrix are included this rises to 97% of the SNPs, however for the sake of computing concordance we try to avoid overestimating concordance by including only the non-Affymetrix submissions to HapMap. This constitutes an excellent resource for the performance evaluation; though it is important to bear in mind the caveat that the genotype calls in HapMap themselves do have some small but non-zero error rate. Additionally, the HapMap samples consist of some trios, enabling the evaluation of Mendelian inheritance error rates. Finally, we also look at reproducibility of genotype calls on sample replicates.

For evaluation of call rates, accuracy and Mendelian inheritance error rate we use four datasets consisting of HapMap samples. The first dataset consists of all 270 HapMap samples, processed jointly by Affymetrix and the Broad Institute. The remaining three sets use a collection of 44 HapMap samples comprising 30 unique DNAs (10 trios) with five of the samples run multiple times to evaluate reproducibility.

To account for the fact that one can adjust the confidence threshold to trade off between call rate and accuracy we look at performance at all possible thresholds and plot the relationship between HapMap concordance and no-call rate, as shown in FIG. 11. Table 1 presents performance for BRLMM-P at its default confidence threshold.

TABLE 1

Performance on HapMap dataset for BRLMM-P at various fixed thresholds. Results are based on 440,794 SNPs.

| Method | Confidence Threshold | Overall Call Rate | Hom Call Rate | Het Call Rate | Overall Concordance | Hom Concordance | Het Concordance |
|---|---|---|---|---|---|---|---|
| DM | 0.26 | 94.16% | 97.24% | 86.32% | 99.15% | 99.39% | 98.38% |
| DM | 0.33 | 95.96% | 98.24% | 90.16% | 98.94% | 99.27% | 97.93% |
| BRLMM | 0.3 | 97.40% | 97.40% | 97.75% | 99.40% | 99.34% | 99.55% |
| BRLMM | 0.4 | 98.27% | 98.30% | 98.48% | 99.31% | 99.25% | 99.47% |
| BRLMM | 0.5 | 98.79% | 98.82% | 98.93% | 99.26% | 99.20% | 99.40% |
| BRLMM | 0.6 | 99.15% | 99.18% | 99.25% | 99.17% | 99.11% | 99.33% |

One caveat about evaluating concordance with HapMap is that to some extent it provides only a lower bound estimate for accuracy, since HapMap itself does have a certain error rate. With this in mind, it is useful to look at additional measures of performance. All four datasets summarized here contain (father, mother, child) trios of samples which can be assessed for Mendelian consistency. The Mendelian consistency is estimated looking only at informative trios (those in which we have a call for all three samples where the parents are not both called heterozygous), call this number T. If the number of such trios which exhibit a Mendelian inconsistency is E then the Mendelian consistency is estimated as (T−E)/3T.

The final metric of performance we evaluate is reproducibility on sample replicates. Arguably this metric is less useful than those above since it only reports on the consistency of calls made but not on whether or not those calls are actually correct. Nevertheless, other things being equal a reproducible method will generally be preferable to one that isn't. The first dataset does not contain replicates, for the other three datasets the pairwise reproducibility of calls is on average 99.9%.

Figure 18:
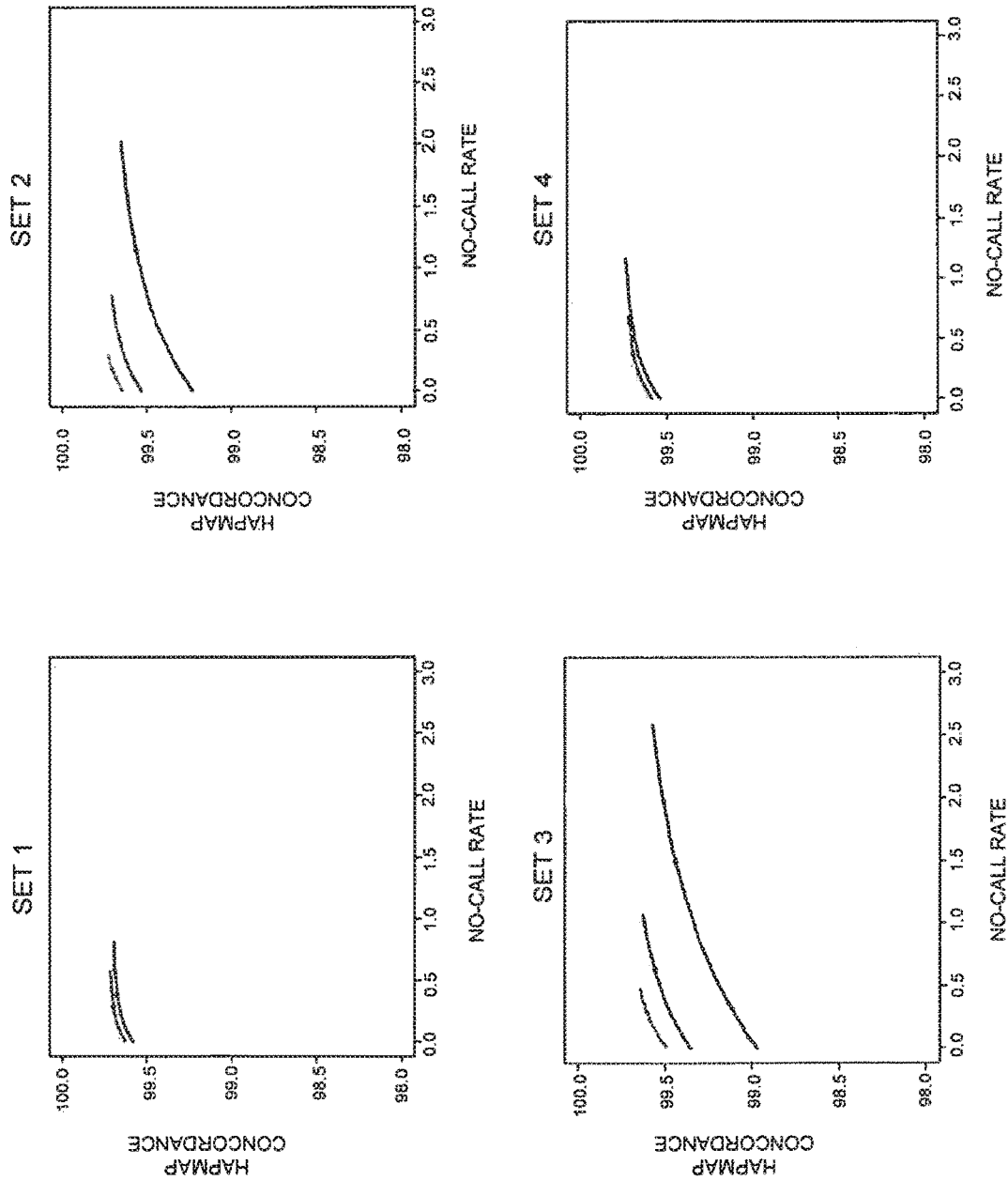
FIG. 18 shows the performance of BRLMM-P on Hap-Map samples.

FIG. 18 shows the performance of BRLMM-P on HapMap samples. Concordance with HapMap and genotype call rate is determined at all possible thresholds, the plots depict the tradeoff between the two performance metrics. The default confidence threshold of 0.5 is indicated as a point on each curve. The red curves present the tradeoff on all genotypes combined, the blue and green curves summarize performance looking only a genotypes that HapMap indicates are heterozygous and homozygous respectively.

BRLMM-P enables accurate calling of genotypes using only PM probes. This allows for more SNPs on an array of a given size. The performance is comparable to the performance of BRLMM on Mapping 500K arrays. As a multiple chip method it has some extra considerations which need to be taken into account in practice.

One matter to consider is the batch size in which to apply BRLMM-P. More samples will generally lead to better performance, however very high performance could be attained with 44 or even fewer samples. Fewer samples could include 30 or fewer, or even 20 or fewer. BRLMM-P performs slightly better on SNPs for which there are observations of all three genotypes. As a result the addition of more samples is expected to be mainly of benefit to SNPs of lower minor allele frequencies, which will be more likely to have only one or two observed genotypes for low number of samples.

Another observation is that reliability of calls improves as the number of observations in the genotype cluster increases. Thus the addition of more samples will tend to be of most benefit to rare genotypes. Since the main benefit is to rarer genotypes, addition of more samples may appear to provide marginal benefit when one focuses on overall performance. Another important consideration is the extent to which datasets can be combined. More samples should improve performance, particularly for rare genotypes. However, the validity of combination of datasets will depend on the degree to which the combined datasets have the same underlying probe intensity distribution and SNP cluster properties. A good way to check the appropriateness of combining datasets is to inspect SNP cluster centers for each dataset separately and to check the degree to which the cluster centers and variances are consistent both with each other and with the SNP specific prior distributions being supplied to BRLMM-P.

Finally, while BRLMM-P removes the reliance on MM probes, it is only one of a variety of genotype calling algorithms that either exist already or are in development. Currently the list of alternatives includes CRLMM [Benilton Carvalho, Terence P. Speed, and Rafael A. Irizarry, "*Exploration, normalization and genotype calls of high density oligonucleotide SNP array data*" (July 2006). Johns Hopkins University, Dept. of Biostatistics Working Papers. Working Paper 111, and GEL [Dan L. Nicolae, Xiaolin Wu, Kazuaki Miyake and Nancy J. Cox "*GEL: a novel genotype calling algorithm using empirical likelihood*" Bioinformatics 22(16), 1942-1947].

Accounting for probe specific effects results in lower variance on allele signal estimates—This step is retained even in arrays employing multiple copies of the same probe, even though the probe specific effects are only minimally different between copies. The distribution of summary values across arrays is then used to evaluate the likely genotypes.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

As will be appreciated by those skilled in the relevant art, the preceding and following descriptions of files generated by applications 372 are exemplary only, and the data described, and other data, may be processed, combined, arranged, and/or presented in many other ways. Also, those of ordinary skill in the related art will appreciate that one or more operations of applications 372 may be performed by software or firmware associated with various instruments. For example, scanner 100 could include a computer that may include a firmware component that performs or controls one or more operations associated with scanner 100.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A method for genotyping a plurality of polymorphisms in a nucleic acid sample, the method comprising:
   hybridizing a nucleic acid sample with a plurality of allele-specific perfect-match probes provided in an array of perfect-match probes for a plurality of target sequences which the array is designed to genotype, wherein, for substantially all of the plurality of target sequences, the array is without corresponding mismatch probes;
   summarizing intensity values associated with the hybridizing to obtain a plurality of signal values, the plurality of signal values comprising a respective signal value for each respective allele of the plurality of polymorphisms;
   transforming the respective signal value for each allele into a space that includes a contrast dimension to obtain a plurality of transformed signal values;
   evaluating likelihood of all plausible divisions of the transformed signal values into seed genotypes to identify most likely plausible divisions;
   averaging over the most likely plausible divisions to derive a plurality of seed genotype clusters; and
   genotyping the plurality of polymorphisms, wherein genotyping comprises comparing the transformed signal values with a set of typical values for each genotype, wherein the set of typical values comprises prior values, wherein the prior values comprise estimates of genotype cluster center locations and genotype cluster center variances of the plurality of seed genotype clusters determined from clustering properties of the transformed signal values;
   wherein the steps of summarizing, transforming, evaluating, averaging, and genotyping are performed on a computer, and wherein the computer comprises a computer processor.

2. The method of claim 1 wherein evaluating likelihood of all plausible divisions comprises applying a Gaussian likelihood model.

3. The method of claim 1, wherein summarizing comprises quantile normalization of the intensity values, and wherein summarizing does not include background adjustment.

4. The method of claim 1, wherein transforming comprises generating a contrast value for each of the signal values, wherein each of the contrast values is associated with a contrast value range.

5. The method of claim 4, wherein the contrast value range of each of the contrast values is between −1 and 1.

6. The method of claim 5, wherein the contrast values that correspond to heterozygous genotypes are stretched, and wherein the contrast values that correspond to homozygous genotypes are compressed.

7. The method of claim 1, wherein the plurality of seed genotype clusters are derived from the clustering properties of the data for each of the plurality of polymorphisms and not in reliance on initial cluster estimates from any mismatch probe analysis.

8. The method of claim 7, wherein the plurality of seed genotype clusters consists of three or fewer seed genotype clusters.

9. The method of claim 7, wherein, for a selected sample or sample portion, the plurality of seed genotype clusters consists of two seed genotype clusters.

10. The method of claim 9 wherein the selected sample or sample portion corresponds to chromosome Y or chromosome X in a male individual from whom the selected sample or sample portion was taken.

11. The method of claim 7, wherein, for a selected sample or sample portion corresponding to chromosome X in a female individual from whom the selected sample or sample portion was taken, the plurality of seed genotype clusters consists of three seed genotype clusters.

12. The method of claim 9 wherein the selected sample or sample portion is a mitochondrial sample or sample portion.

13. The method of claim 7, wherein each of the transformed signal values is assigned to exactly one of the plurality of seed genotype clusters, thereby generating a plurality of initial assignments.

14. The method of claim 13, wherein the plurality of initial assignments is evaluated under a Gaussian cluster model, thereby generating a plurality of final assignments.

15. The method of claim 14, wherein each of the plurality of final assignments is combined with the transformed signal values to generate a posterior distribution of genotype clusters.

16. The method of claim 1, wherein the plausible divisions are determined by restricting possible clusters to an expected number of genotypes of increasing contrast.

17. The method of claim 16, wherein the plausible divisions are determined by restricting possible clusters to an expected number of genotypes of increasing contrast, with a minimum distance allowed between cluster centers.

18. The method of claim 1, further comprising:
   evaluating the likelihood for each plausible assignment of seed genotypes based on a posterior likelihood of the clusters;

from the likelihoods of all assignments, computing a relative probability assignment for each transformed signal value to be assigned as each genotype;

computing a posterior distribution of centers and spread for each genotype using the resulting relative probability assignment to seed the final computation; and determining genotypes and confidences for each SNP using the posterior distribution of centers and spread for each genotype.

19. The method of claim 1, wherein transforming the signal values increases contrast between seed genotype clusters and provides a genotype order relation that holds between cluster centers.

20. The method of claim 19, wherein the genotype order relation is of the form BB left of AB left of AA, and wherein the genotype order relation is required of all fits to the data.

21. The method of claim 1, further comprising:

by using a Bayesian procedure, combining a prior estimate of genotype cluster centers and variances for each polymorphism with the transformed signal values and genotype seed assignments for the transformed signal values determined from the cluster properties of the transformed signal values to obtain a posterior estimate of cluster centers and variances;

calling genotypes of the transformed signal values for a polymorphism using the posterior estimate.

22. The method of claim 21, wherein determining genotype seed assignments for a polymorphism comprises:

determining the likelihood for all plausible seed genotype clusters of the transformed signal values and averaging over the most likely seeds.

23. The method of claim 22, wherein determining the likelihood for all plausible seed genotype clusters of the transformed signal values and averaging over the most likely seeds further comprises:

repeatedly assigning each of the transformed signal values to seed genotype clusters, wherein each transformed signal value is assigned to exactly one seed genotype cluster resulting in a plausible hard assignment for each transformed signal value;

evaluating the likelihood of each plausible hard assignment under a Gaussian cluster model to evaluate the quality of the hard assignment;

combining most likely plausible hard assignments into a soft assignment that allows transformed signal values to be partially assigned to more than one seed genotype cluster; and using this soft assignment of genotypes as a reliable seed.

24. The method of claim 22, wherein the plausible seed genotype clusters are assigned based on two dividing contrast values corresponding to vertical lines in contrast that determine the transitions between genotypes.

25. The method of claim 1, further comprising: restricting a weighting of cluster centers and variances from prior values in order to accommodate potential shifting of the cluster centers in the transformed signal values.

26. The method of claim 1, further comprising: controlling the amount of mixing between cluster centers by counting transformed signal values in each cluster more towards the estimate of that cluster, without requiring all clusters to have the same variance.

27. The method of claim 1, further comprising: applying a likelihood penalty for each cluster observed to reduce clusters from erroneously splitting.

28. The method of claim 1, further comprising: applying a likelihood penalty for assignments to a cluster based on the frequency of data in that cluster to reduce erroneously assigning transformed signal data to clusters with low frequency.

29. The method of claim 1 wherein the plurality of polymorphisms comprises single nucleotide polymorphisms (SNPs).

* * * * *